(12) United States Patent
Xue et al.

(10) Patent No.: US 11,136,253 B1
(45) Date of Patent: Oct. 5, 2021

(54) MICROBIOLOGICAL TREATMENT SYSTEM FOR ETHYLENE OXIDE EXHAUST GAS

(71) Applicants: Chio Kang Medical, Inc., Palo Alto, CA (US); QIAOKANG BIOTECH (GUANGDONG) CO., LTD, Guangzhou (CN)

(72) Inventors: Jianlong Xue, Guangzhou (CN); Shengwei Hu, Guangzhou (CN); Dongxin Hou, Guangzhou (CN); Yecheng He, Guangzhou (CN); Hao Chen, Guangzhou (CN); Ziping Zhu, Guangzhou (CN); Qinghua Xiao, Guangzhou (CN); Lixiong Feng, Guangzhou (CN)

(73) Assignees: Chio Kang Medical, Inc., Palo Alto, CA (US); Qiaokang Biotech (Guangdong) Co., LTD., Guangzhou (CN)

(*) Notice: Subject to any disclaimer, the term of this patent is extended or adjusted under 35 U.S.C. 154(b) by 0 days.

(21) Appl. No.: 17/012,864

(22) Filed: Sep. 4, 2020

Related U.S. Application Data

(63) Continuation of application No. PCT/CN2020/101142, filed on Jul. 9, 2020.

(30) Foreign Application Priority Data

Mar. 18, 2020 (CN) .......................... 202010190370.1
Mar. 18, 2020 (CN) .......................... 202020340594.1
(Continued)

(51) Int. Cl.
C02F 3/34 (2006.01)
B01D 53/14 (2006.01)
(Continued)

(52) U.S. Cl.
CPC ............ *C02F 3/34* (2013.01); *B01D 53/0438* (2013.01); *B01D 53/1487* (2013.01);
(Continued)

(58) Field of Classification Search
CPC ...... C02F 3/34; C02F 9/00; C02F 3/30; C02F 2103/18; C02F 2101/34; C12N 1/20;
(Continued)

(56) References Cited

U.S. PATENT DOCUMENTS 1,954,056 A 4/1934 Miller
2,586,670 A 2/1952 Lambertsen
(Continued)

FOREIGN PATENT DOCUMENTS

CN 1223166 A 7/1999
CN 1397474 A 2/2003
(Continued)

OTHER PUBLICATIONS

U.S. Appl. No. 17/012,857, Notice of Allowance, dated Mar. 1, 2021, 26 pages.
(Continued)

Primary Examiner — Fred Prince
(74) Attorney, Agent, or Firm — Adsero IP

(57) ABSTRACT

The present disclosure provides a microbiological treatment system including a hydration system and microbiological degradation systems. The hydration system may include a gas-liquid mixing chamber, a gas inlet, a gas outlet, a liquid inlet, and a liquid outlet, the latter four being fluidly coupled to the chamber. The gas inlet is configured to introduce an ethylene oxide exhaust gas into the chamber to mix with an aqueous solution to form an ethylene oxide exhaust liquor. The liquid outlet is configured to discharge the ethylene oxide exhaust liquor. Each microbiological degradation system may include a degradation chamber containing degra-
(Continued)

dation bacteria including one of anaerobic bacteria, facultative bacteria, or aerobic bacteria. The degradation chambers of the microbiological degradation systems may be in fluid communication sequentially in a predetermined degradation sequence, with the most upstream in the degradation sequence having a liquid inlet in fluid communication with the liquid outlet.

18 Claims, 2 Drawing Sheets

Specification includes a Sequence Listing.

(30) Foreign Application Priority Data

Mar. 19, 2020 (CN) .................. 202010194457.6
Mar. 19, 2020 (CN) .................. 202020348776.3

(51) Int. Cl.
```
B01D 53/18      (2006.01)
B01D 53/04      (2006.01)
C02F 3/30       (2006.01)
C02F 9/00       (2006.01)
B01D 53/84      (2006.01)
C12N 1/32       (2006.01)
C12N 1/20       (2006.01)
C02F 103/18     (2006.01)
C02F 101/34     (2006.01)
```
(52) U.S. Cl.
CPC ....... *B01D 53/1493* (2013.01); *B01D 53/185* (2013.01); *B01D 53/84* (2013.01); *C02F 3/30* (2013.01); *C02F 9/00* (2013.01); *C12N 1/20* (2013.01); *C12N 1/32* (2013.01); *B01D 53/04* (2013.01); *B01D 2252/103* (2013.01); *B01D 2253/102* (2013.01); *B01D 2257/708* (2013.01); *C02F 2101/34* (2013.01); *C02F 2103/18* (2013.01)

(58) Field of Classification Search
CPC ...... C12N 1/32; B01D 53/84; B01D 53/0438; B01D 353/185; B01D 53/1487; B01D 53/1493; B01D 53/04; B01D 2257/708; B01D 2252/103; B01D 2253/102
USPC ..... 210/605; 95/149, 240, 901; 96/108, 243, 96/329; 435/283.1, 289.1
See application file for complete search history.

(56) References Cited

U.S. PATENT DOCUMENTS

| | | | |
|---|---|---|---|
| 2,817,689 A | 12/1957 | White | |
| 3,022,054 A | 2/1962 | Kotzebue | |
| 3,598,543 A | 6/1969 | Crosby et al. | |
| 3,572,391 A | 3/1971 | Hirsch et al. | |
| 3,844,739 A | 10/1974 | Alfrey, Jr. | |
| 3,961,920 A | 6/1976 | Gilbert | |
| 3,997,633 A | 12/1976 | Leva et al. | |
| 4,112,054 A | 9/1978 | Feingold et al. | |
| 4,119,539 A | 10/1978 | Ettel et al. | |
| 4,134,425 A | 1/1979 | Gussefeld et al. | |
| 4,243,636 A | 1/1981 | Shiraki et al. | |
| 4,301,113 A | 11/1981 | Alguire et al. | |
| 4,517,167 A | 5/1985 | Popescu et al. | |
| 4,549,363 A | 10/1985 | Buonicore | |
| 4,555,251 A * | 11/1985 | Jonsson | C07D 301/32 422/34 |
| 4,831,196 A | 5/1989 | Buonicore et al. | |
| 5,084,075 A | 1/1992 | Sircar | |
| 5,204,075 A | 4/1993 | Jain et al. | |
| 5,270,000 A | 12/1993 | Goldner et al. | |
| 5,283,035 A | 2/1994 | Karthaus et al. | |
| 5,290,345 A | 3/1994 | Osendorf et al. | |
| 5,511,409 A | 4/1996 | Knaebel | |
| 5,522,808 A | 6/1996 | Skalla | |
| 5,607,652 A | 3/1997 | Hellmuth et al. | |
| 5,641,455 A | 6/1997 | Rosenlund et al. | |
| 5,702,669 A | 12/1997 | Green et al. | |
| 5,741,470 A | 4/1998 | Wenzler | |
| 5,755,857 A | 5/1998 | Acharya et al. | |
| 5,779,773 A | 7/1998 | Cam et al. | |
| 5,964,927 A | 10/1999 | Graham et al. | |
| 6,156,101 A | 12/2000 | Naheiri | |
| 6,684,648 B2 | 2/2004 | Faqih | |
| 6,743,402 B2 | 6/2004 | Shimakawa | |
| 7,316,733 B1 | 1/2008 | Hedrick | |
| 7,625,535 B2 | 12/2009 | Yamaguchi | |
| 8,110,156 B2 | 2/2012 | Ricciardi et al. | |
| 8,431,085 B2 | 4/2013 | Froderberg et al. | |
| 9,616,143 B2 | 4/2017 | Snyder et al. | |
| 10,987,443 B1 | 4/2021 | Hu et al. | |
| 2002/0046569 A1 | 4/2002 | Faqih | |
| 2002/0197194 A1 | 12/2002 | Machado et al. | |
| 2005/0145108 A1* | 7/2005 | Rubin | B01D 53/78 95/226 |
| 2006/0236860 A1 | 10/2006 | Sumida et al. | |
| 2006/0249027 A1 | 11/2006 | Adolphsen et al. | |
| 2007/0209383 A1 | 9/2007 | Hutton | |
| 2008/0078289 A1 | 4/2008 | Sergi et al. | |
| 2008/0080999 A1 | 4/2008 | Bondar | |
| 2008/0289591 A1 | 11/2008 | Tessier et al. | |
| 2010/0196194 A1 | 8/2010 | Voeten et al. | |
| 2011/0265644 A1 | 11/2011 | Swami et al. | |
| 2011/0283885 A1* | 11/2011 | Thiele | B01D 53/1475 95/199 |
| 2012/0031268 A1 | 2/2012 | Yaghi et al. | |
| 2012/0298207 A1 | 11/2012 | Woelk et al. | |
| 2014/0119989 A1 | 5/2014 | Hayashi | |
| 2014/0251130 A1 | 9/2014 | Sprinkle et al. | |
| 2014/0290162 A1 | 10/2014 | Tanimoto | |
| 2016/0010883 A1 | 1/2016 | Jomitz et al. | |
| 2017/0056813 A1 | 3/2017 | McMahon et al. | |
| 2019/0076776 A1 | 3/2019 | Mahecha-Botero et al. | |
| 2019/0151791 A1 | 5/2019 | Awadh et al. | |
| 2019/0175971 A1 | 6/2019 | Moore et al. | |
| 2020/0148655 A1 | 5/2020 | Duff et al. | |

FOREIGN PATENT DOCUMENTS

| | | |
|---|---|---|
| CN | 101224381 A | 7/2008 |
| CN | 101549241 A | 10/2009 |
| CN | 101773762 A | 7/2010 |
| CN | 201632182 U | 11/2010 |
| CN | 102173384 A | 9/2011 |
| CN | 102219642 A | 10/2011 |
| CN | 102302791 A | 1/2012 |
| CN | 102921570 A | 2/2013 |
| CN | 202802975 U | 3/2013 |
| CN | 202933710 U | 5/2013 |
| CN | 203183363 U | 9/2013 |
| CN | 103386141 A | 11/2013 |
| CN | 103394109 A | 11/2013 |
| CN | 103394278 A | 11/2013 |
| CN | 103657383 A | 3/2014 |
| CN | 103706233 A | 4/2014 |
| CN | 203507806 U | 4/2014 |
| CN | 203564952 U | 4/2014 |
| CN | 103800926 A | 5/2014 |
| CN | 103908688 A | 7/2014 |
| CN | 203749877 U | 8/2014 |
| CN | 203750388 U | 8/2014 |
| CN | 203750389 U | 8/2014 |
| CN | 104014227 A | 9/2014 |
| CN | 104275085 A | 1/2015 |
| CN | 104307008 A | 1/2015 |
| CN | 204261680 U | 4/2015 |
| CN | 204447972 U | 7/2015 |
| CN | 104815535 A | 8/2015 |
| CN | 105132060 A | 12/2015 |

(56) References Cited

FOREIGN PATENT DOCUMENTS

| | | | |
|---|---|---|---|
| CN | 105327665 A | 2/2016 | |
| CN | 105664822 A | 2/2016 | |
| CN | 205300112 U | 6/2016 | |
| CN | 210721130 U | 6/2016 | |
| CN | 106139199 A | 11/2016 | |
| CN | 106421844 A | 2/2017 | |
| CN | 106475021 A | 3/2017 | |
| CN | 106582126 A | 4/2017 | |
| CN | 206443946 U | 8/2017 | |
| CN | 206535551 U | 10/2017 | |
| CN | 206853397 U | 1/2018 | |
| CN | 107677016 A | 2/2018 | |
| CN | 207169397 U | 4/2018 | |
| CN | 207187436 U | 4/2018 | |
| CN | 207356290 U | 5/2018 | |
| CN | 207745676 U | 8/2018 | |
| CN | 207913454 U | 9/2018 | |
| CN | 108607511 A | 10/2018 | |
| CN | 208047841 U | 11/2018 | |
| CN | 208218734 U | 12/2018 | |
| CN | 109382064 A | 2/2019 | |
| CN | 208448985 U | 2/2019 | |
| CN | 208893903 U | 5/2019 | |
| CN | 110145747 A | 8/2019 | |
| CN | 110302634 A | 10/2019 | |
| CN | 110404485 A | 11/2019 | |
| CN | 110461371 A | 11/2019 | |
| CN | 209662917 U | 11/2019 | |
| CN | 110833754 A | 2/2020 | |
| CN | 210021633 U | 2/2020 | |
| CN | 210088451 U | 2/2020 | |
| DE | 4236622 C1 | 3/1994 | |
| EP | 0130319 A2 | 1/1985 | |
| EP | 0350677 A1 | 1/1990 | |
| EP | 1302478 A1 | 4/2003 | |
| EP | 2883598 A1 | 6/2015 | |
| GB | 1472091 A | 4/1977 | |
| JP | 2008114210 A | 5/2008 | |
| JP | 2013172790 A | 10/2016 | |
| JP | 2010259648 A | 5/2018 | |
| WO | WO 92/20432 A2 * | 11/1992 | |
| WO | WO2011002277 A1 | 1/2011 | |
| WO | WO-2019-136504 A1 | 7/2019 | |
| WO | WO2019236249 A1 | 12/2019 | |

OTHER PUBLICATIONS

U.S. Appl. No. 17/002,540, Final Office Action, dated Mar. 26, 2021, 36 pages.
U.S. Appl. No. 17/004,730, Non-Final Office Action, dated Apr. 1, 2021, 30 pages.
U.S. Appl. No. 17/002,500, Non-Final Office Action dated Apr. 14, 2021, 89 pages.
U.S. Appl. No. 17/002,540, Notice of Allowance, dated Apr. 26, 2021, 21 pages.
International Search Report & Written Opinion for PCT/CN2020/100113 as prepared by the Chinese International Searching Authority dated Mar. 31, 2021, 10 pages.
International Search Report & Written Opinion for PCT/CN2020/100122 as prepared by the Chinese International Searching Authority dated Mar. 26, 2021, 11 pages.
International Search Report & Written Opinion for PCT/CN2020/100120 as prepared by the Chinese International Searching Authority dated Mar. 31, 2021,10 pages.
U.S. Appl. No. 17/004,930 Notice of Allowance, dated Apr. 28, 2020, 35 pages.
U.S. Appl. No. 17/004,903 Notice of Allowance, dated May 17, 2021, 20 pages.
U.S. Appl. No. 17/002,529 Notice of Allowance, dated May 3, 2021, 30 pages.
U.S. Appl. No. 17/002,523 Notice of Allowance, dated May 27, 2021, 26 pages.
U.S. Appl. No. 17/012,857, Non-Final Office Action, dated Nov. 24, 2020, 13 pages.
U.S. Appl. No. 17/002,540, Office Action—Restriction Requirement, dated Dec. 1, 2020, 7 pages.
U.S. Appl. No. 17/002,500, Non-Final Office Action dated Dec. 8, 2020, 109 pages.
Kahm et al., 2018 "Lyapunov exponents with Model Predictive Control for exothermic batch reactors" IFAC—PapersOnline, 51, 417-422.
U.S. Appl. No. 17/004,971, Office Action—Restriction Requirement, dated Dec. 9, 2020, 6 pages.
U.S. Appl. No. 17/002,523 Notice of Allowance, dated Dec. 17, 2020, 35 pages.
U.S. Appl. No. 17/004,930 Office Action—Restriction Requirement, dated Dec. 18, 2020, 8 pages.
U.S. Appl. No. 17/002,540, Non-Final Office Action dated Dec. 30, 2020, 62 pages.
U.S. Appl. No. 17/004,930 Non-Final Office Action dated Jan. 26, 2021, 28 pages.
International Search Report and Written Opinion, International Application No. PCT/CN2020/101140 dated Dec. 21, 2020, 11 pages.
International Search Report and Written Opinion, International Application No. PCT/CN2020/100143 dated Dec. 21, 2020, 9 pages.
International Search Report and Written Opinion, International Application No. PCT/CN2020/100125 dated Dec. 23, 2020, 9 pages.
International Search Report and Written Opinion, International Application No. PCT/CN2020/100115 dated Dec. 16, 2020, 11 pages.
International Search Report and Written Opinion, International Application No. PCT/CN2020/100119 dated Dec. 17, 2020, 9 pages.
International Search Report and Written Opinion, International Application No. PCT/CN2020/101142 dated Dec. 16, 2020, 11 pages.
International Search Report and Written Opinion, International Application No. PCT/CN2020/100144 dated Dec. 18, 2020, 10 pages.
U.S. Appl. No. 17/002,500, Final Office Action dated Feb. 8, 2021, 57 pages.
U.S. Appl. No. 17/004,971, Notice of Allowance, dated Feb. 8, 2021, 30 pages.
U.S. Appl. No. 17/002,529, Non-Final Office Action—Restriction Requirement dated Feb. 17, 2021, 11 pages.
International Application No. PCT/CN2020/101140 as prepared by the Chinese International Searching Authority filed on Jul. 9, 2020, 59 pages.
U.S. Appl.No. 17/012,857, TrackOne Bypass CON Application filed Sep. 4, 2020, 148 pages.
International Application No. PCT/CN2020/100143 as prepared by the Chinese International Searching Authority filed on Jul. 3, 2020, 25 pages.
U.S. Appl. No. 17/002,500, TrackOne Bypass CON Application filed Aug. 25, 2020, 61 pages.
International Application No. PCT/CN2020/100125 as prepared by the Chinese International Searching Authority filed on Jul. 3, 2020, 27 pages.
U.S. Appl. No. 17/002,523, TrackOne Bypass CON Application filed Aug. 25, 2020, 72 pages.
U.S. Appl. No. 17/002,523 Non-Final Office Action, dated Oct. 27, 2020, 54 pages.
International Application No. PCT/CN2020/100115 as prepared by the Chinese International Searching Authority filed on Jul. 3, 2020, 22 pages.
U.S. Appl. No. 17/002,529, TrackOne Bypass CON Application filed Aug. 25, 2020, 64 pages.
International Application No. PCT/CN2020/100119 as prepared by the Chinese International Searching Authority filed on Jul. 3, 2020, 29 pages.
U.S. Appl. No. 17/002,540, TrackOne Bypass CON Application filed Aug. 25, 2020, 89 pages.

(56) References Cited

OTHER PUBLICATIONS

International Application No. PCT/CN2020/100120 as prepared by the Chinese International Searching Authority filed on Jul. 3, 2020, 28 pages.
U.S. Appl. No. 17/004,730, TrackOne Bypass CON Application filed Aug. 27, 2020, 77 pages.
International Application No. PCT/CN2020/101142 as prepared by the Chinese International Searching Authority filed on Jul. 9, 2020, 29 pages.
International Application No. PCT/CN2020/100144 as prepared by the Chinese International Searching Authority filed on Jul. 3, 2020, 24 pages.
U.S. Appl. No. 17/004,903, TrackOne Bypass CON Application filed Aug. 27, 2020, 67 pages.
U.S. Appl. No. 17/004,903 Notice of Allowance, dated Nov. 6, 2020, 19 pages.
International Application No. PCT/CN2020/100122 as prepared by the Chinese International Searching Authority filed on Jul. 3, 2020, 34 pages.
U.S. Appl. No. 17/004,930, TrackOne Bypass CON Application filed Aug. 27, 2020, 80 pages.
U.S. Appl. No. 17/004,930 Office Action—Restriction Requirement, dated Nov. 4, 2020, 6 pages.
International Application No. PCT/CN2020/100113 as prepared by the Chinese International Searching Authority filed on Jul. 3, 2020, 35 pages.
U.S. Appl. No. 17/004,971, TrackOne Bypass CON Application filed Aug. 27, 2020, 75 pages.
U.S. Appl. No. 17/004,730, Notice of Allowance, dated Jun. 24, 2021, 30 pages.
U.S. Appl. No. 17/012,857, Notice of Allowance, dated Jun. 28, 2021, 21 pages.
U.S. Appl. No. 17/002,500, Notice of Allowance dated Jul. 8, 2021, 27 pages.

* cited by examiner

SEQUENCE LISTING

```
<160> NUMBER OF SEQ ID NOS: 10

<210> SEQ ID NO 1
<211> LENGTH: 1432
<212> TYPE: DNA
<213> ORGANISM: Alcaligenes faecalis

<400> SEQUENCE: 1
gctttaacac atgcaagtcg aacggcagca cgcagagagc ttgctctctt ggtggcgagt      60
ggcggacggg tgagtaatat atcggaacgt gcccagtagc gggggataac tactcgaaag     120
agtggctaat accgcatacg ccctacgggg gaaaggggg gatcgcaaga cctctcacta      180
ttggagcggc cgatatcgga ttagctagtt ggtggggtaa aggctcacca aggcaacgat     240
ccgtagctgg tttgagagga cgaccagcca cactgggact gagacacggc ccagactcct     300
acgggaggca gcagtgggga attttggaca atggggggaaa ccctgatcca gccatcccgc     360
gtgtatgatg aaggccttcg ggttgtaaag tacttttggc agagaagaaa aggcatcccc     420
taatacggga tgctgctgac ggtatctgca gaataagcac cggctaacta cgtgccagca     480
gccgcggtaa tacgtagggt gcaagcgtta atcggaatta ctgggcgtaa agcgtgtgta     540
```

-continued

```
ggcggttcgg aaagaaagat gtgaaatccc agggctcaac cttggaactg catttttaac     600
tgccgagcta gagtatgtca gaggggggta gaattccacg tgtagcagtg aaatgcgtag     660
atatgtggag gaataccgat ggcgaaggca gccccctggg ataatactga cgctcagaca     720
cgaaagcgtg gggagcaaac aggattagat accctggtag tccacgccct aaacgatgtc     780
aactagctgt tggggccgtt aggccttagt agcgcagcta acgcgtgaag ttgaccgcct     840
ggggagtacg gtcgcaagat taaaactcaa aggaattgac ggggacccgc acaagcggtg     900
gatgatgtgg attaattcga tgcaacgcga aaaaccttac ctacccttga catgtctgga     960
aagccgaaga gatttggcag tgctcgcaag agaaccggaa cacaggtgct gcatggctgt    1020
cgtcagctcg tgtcgtgaga tgttgggtta agtcccgcaa cgagcgcaac ccttgtcatt    1080
agttgctacg caagagcact ctaatgagac tgccggtgac aaaccggagg aaggtgggga    1140
tgacgtcaag tcctcatggc ccttatgggt agggcttcac acgtcataca atggtcggga    1200
cagagggtcg ccaacccgcg agggggagcc aatctcagaa acccgatcgt agtccggatc    1260
gcagtctgca actcgactgc gtgaagtcgg aatcgctagt aatcgcggat cagaatgtcg    1320
cggtgaatac gttcccgggt cttgtacaca ccgcccgtca caccatggga gtgggtttca    1380
ccagaagtag gtagcctaac cgcaaggagg gcgctaccac ggtgatgatg tc            1432
```

```

<210> SEQ ID NO 2
<211> LENGTH: 1412
<212> TYPE: DNA
<213> ORGANISM: Acetobacter peroxydans

<400> SEQUENCE: 2

```

```
agagtttgat catggctcag agcgaacgct ggcggcatgc ttaacacatg caagtcgcac      60
gaaggtttcg gccttagtgg cggacgggtg agtaacgcgt aggaatctat ccatgggtgg     120
gggataacac tgggaaactg gtgctaatac cgcatgacac ctgagggtca aaggcgcaag     180
tcgcctgtgg aggagcctgc gttcgattag ctagttggtg gggtaaaggc ctaccaaggc     240
gatgatcgat agctggtttg agaggatgat cagccacact gggactgaga cacggcccag     300
actcctacgg gaggcagcag tggggaatat tggacaatgg gggcaaccct gatccagcaa     360
tgccgcgtgt gtgaagaagg tcttcggatt gtaaagcact ttcgacgggg acgatgatga     420
cggtacccgt agaagaagcc ccggctaact tcgtgccagc agccgcggta atacgaaggg     480
ggctagcgtt gctcggaatg actgggcgta aagggcgtgt aggcggtttt gacagtcaga     540
tgtgaaatcc ccgggcttaa cctgggagct gcatttgaga cgttaagact agagtgtgag     600
agagggttgt ggaattccca gtgtagaggt gaaattcgta gatattggga agaacaccgg     660
tggcgaaggc ggcaacctgg ctcattactg acgctgaggc gcgaaagcgt ggggagcaaa     720
caggattaga taccctggta gtccacgctg taaacgatgt gtgctagatg ttgggtaact     780
tagttactca gtgtcgcagt taacgcgtta agcacaccgc ctggggagta cggccgcaag     840
gttgaaactc aaaggaattg acgggggccc gcacaagcgg tggagcatgt ggtttaattc     900
gaagcaacgc gcagaacctt accagggctt gaatgtggag gctgtaggca gagatgtcta     960
tttcttcgga cctccaacac aggtgctgca tggctgtcgt cagctcgtgt cgtgagatgt    1020
tgggttaagt cccgcaacga gcgcaacccc tatctttagt tgccagcatg tttgggtggg    1080
cactctagag agactgccgg tgacaagccg gaggaaggtg gggatgacgt caagtcctca    1140
tggcccttat gtcctgggct acacacgtgc tacaatggcg gtgacagtgg gaagctatgt    1200
ggtgacacag tgctgatctc taaaagccgt ctcagttcgg attgcactct gcaactcgag    1260
```

-continued

| | |
|---|---|
| tgcatgaagg tggaatcgct agtaatcgcg gatcagcatg ccgcggtgaa tacgttcccg | 1320 |
| ggccttgtac acaccgcccg tcacaccatg ggagtggttt gaccttaagc cggtgagcga | 1380 |
| accgcaagga cgcagccgac cacgtcgtcg ct | 1412 |

<210> SEQ ID NO 3
<211> LENGTH: 1453
<212> TYPE: DNA
<213> ORGANISM: Lactobacillus fermentum

<400> SEQUENCE: 3

| | |
|---|---|
| gcggctggct cctaaaaggt taccccaccg actttgggtg ttacaaactc tcatggtgtg | 60 |
| acgggcggtg tgtacaaggc ccgggaacgt attcaccgcg gcatgctgat ccgcgattac | 120 |
| tagcgattcc gacttcgtgc aggcgagttg cagcctgcag tccgaactga aacggttttt | 180 |
| aagagatttg cttgccctcg cgagttcgcg actcgttgta ccgtccattg tagcacgtgt | 240 |
| gtagcccagg tcataagggg catgatgatc tgacgtcgtc cccaccttcc tccggtttgt | 300 |
| caccggcagt ctcactagag tgcccaactt aatgctggca actagtaaca agggttgcgc | 360 |
| tcgttgcggg acttaaccca acatctcacg cacgagctg acgacgacca tgcaccacct | 420 |
| gtcattgcgt tcccgaagga aacgccctat ctctagggtt ggcgcaagat gtcaagacct | 480 |
| ggtaaggttc ttcgcgtagc ttcgaattaa accacatgct ccaccgcttg tgcgggcccc | 540 |
| cgtcaattcc tttgagtttc aaccttgcgg tcgtactccc caggcggagt gcttaatgcg | 600 |
| ttagctccgg cactgaaggg cggaaaccct ccaacaccta gcactcatcg tttacggcat | 660 |
| ggactaccag ggtatctaat cctgttcgct acccatgctt tcgagtctca gcgtcagttg | 720 |
| cagaccaggt agccgccttc gccactggtg ttcttccata tatctacgca ttccaccgct | 780 |
| acacatggag ttccactacc ctcttctgca ctcaagttat ccagtttccg atgcacttct | 840 |
| ccggttaagc cgaaggcttt cacatcgac ttagaaaacc gcctgcactc tctttacgcc | 900 |
| caataaatcc ggataacgct tgccacctac gtattaccgc ggctgctggc acgtagttag | 960 |
| ccgtgacttt ctggttaaat accgtcaacg tatgaacagt tactctcata cgtgttcttc | 1020 |
| tttaacaaca gagctttacg agccgaaacc cttcttcact cacgcggtgt tgctccatca | 1080 |
| ggcttgcgcc cattgtggaa gattccctac tgctgcctcc cgtaggagta tgggccgtgt | 1140 |
| ctcagtccca ttgtggccga tcagtctctc aactcggcta tgcatcatcg ccttggtagg | 1200 |
| ccgttacccc accaacaagc taatgcaccg caggtccatc cagaagtgat agcgagaagc | 1260 |
| catcttttaa gcgttgttca tcgaacaac gctgttatgc ggtattagca tctgtttcca | 1320 |
| aatgttgtcc cccgcttctg ggcaggttac ctacgtgtta ctcacccgtc cgccactcgt | 1380 |
| tggcgaccaa aatcaatcag gtgcaagcac catcaatcaa ttgggccaac gcgttcgact | 1440 |
| gcattattag gca | 1453 |

<210> SEQ ID NO 4
<211> LENGTH: 1439
<212> TYPE: DNA
<213> ORGANISM: Bacillus subtilis

<400> SEQUENCE: 4

| | |
|---|---|
| ctatacatgc aagtcgagcg gacagatggg agcttgctcc ctgatgttag cggcggacgg | 60 |
| gtgagtaaca cgtgggtaac ctgcctgtaa gactgggata actccgggaa accggggcta | 120 |
| ataccggatg gttgtttgaa ccgcatggtt cagacataaa aggtggcttc ggctaccact | 180 |

```
tacagatgga  cccgcggcgc  attagctagt  tggtgaggta  acggctcacc  aaggcgacga    240
tgcgtagccg  acctgagagg  gtgatcggcc  acactgggac  tgagacacgg  cccagactcc    300
tacgggaggc  agcagtaggg  aatcttccgc  aatggacgaa  agtctgacgg  agcaacgccg    360
cgtgagtgat  gaaggttttc  ggatcgtaaa  gctctgttgt  tagggaagaa  caagtgccgt    420
tcaaataggg  cggcaccttg  acggtaccta  accagaaagc  cacggctaac  tacgtgccag    480
cagccgcggt  aatacgtagg  tgcaagcgt  tgtccggaat  tattgggcgt  aaagggctcg    540
caggcggttt  cttaagtctg  atgtgaaagc  ccccggctca  accggggagg  gtcattggaa    600 actgggaac  ttgagtgcag  aagaggagag  tggaattcca  cgtgtagcgg  tgaaatgcgt    660
agagatgtgg  aggaacacca  gtggcgaagg  cgactctctg  gtctgtaact  gacgctgagg    720
agcgaaagcg  tggggagcga  acaggattag  ataccctggt  agtccacgcc  gtaaacgatg    780
agtgctaagt  gttagggggt  tccgcccct  tagtgctgca  gctaacgcat  taagcactcc    840
gcctggggag  tacggtcgca  agactgaaac  tcaaaggaat  tgacgggggc  ccgcacaagc    900
ggtggagcat  gtggtttaat  tcgaagcaac  gcgaagaacc  ttaccaggtc  ttgacatcct    960
ctgacaatcc  tagagatagg  acgtcccctt  cgggggcaga  gtgacaggtg  gtgcatggtt   1020
gtcgtcagct  cgtgtcgtga  gatgttgggt  taagtcccgc  aacgagcgca  acccttgatc   1080
ttagttgcca  gcattcagtt  gggcactcta  aggtgactgc  cggtgacaaa  ccggaggaag   1140
gtggggatga  cgtcaaatca  tcatgcccct  tatgacctgg  gctacacacg  tgctacaatg   1200
ggcagaacaa  agggcagcga  aaccgcgagg  ttaagccaat  cccacaaatc  tgttctcagt   1260
tcggatcgca  gtctgcaact  cgactgcgtg  aagctggaat  cgctagtaat  cgcggatcag   1320
catgccgcgg  tgaatacgtt  cccgggcctt  gtacacaccg  cccgtcacac  cacgagagtt   1380
tgtaacaccc  gaagtcggtg  aggtaacctt  ttaggagcca  gccgccgaag  gttggacag    1439

<210> SEQ ID NO 5
<211> LENGTH: 1430
<212> TYPE: DNA
<213> ORGANISM: Kurthia gibsonii

<400> SEQUENCE: 5
ctatacatgc  agtcgagcga  atgacgagaa  gcttgcttct  ctgatttagc  ggcggacggg     60
tgagtaacac  gtgggcaacc  tgccctacag  atcgggataa  ctcagggaaa  cctgggctaa    120
taccggataa  tccttcgaat  cacatgtttt  gaagttgaaa  ggcgcttcgg  cgtcactgta    180
ggatgggccc  gcggtgcatt  agctagttgg  tggggtaacg  gcctaccaag  gcaacgatgc    240
atagccgacc  tgagagggtg  atcggccaca  ttgggactga  gacacggccc  aaactcctac    300
gggaggcagc  agtagggaat  cttccacaat  ggacgaaagt  ctgatggagc  aacgccgcgt    360
gagtgatgaa  ggttttcgga  tcgtaaaact  ctgttgtaag  ggaagaacaa  gtacgttagg    420
aaatgaacgt  accttgacgg  taccttatta  gaaagccacg  gctaactacg  tgccagcagc    480
cgcggtaata  cgtaggtggc  aagcgttgtc  cggatttatt  gggcgtaaag  cgcgcgcagg    540
tggtttctta  agtctgatgt  gaaagcccac  ggctcaaccg  tggagggtca  ttggaaactg    600
gggaacttga  gtgcagaaga  ggatagtgga  attccaagtg  tagcggtgaa  atgcgtagag    660
atttggagga  acaccagtgg  cgaaggcgac  tgtctggtct  gtaactgaca  ctgaggcgcg    720
aaagcgtggg  gagcaaacag  gattagatac  cctggtagtc  cacgccgtaa  acgatgagtg    780
ctaagtgtta  ggggtttcc  gccccttagt  gctgcagcta  acgcattaag  cactccgcct    840
ggggagtacg  accgcaaggt  tgaaactcaa  aggaattgac  gggggcccgc  acaagcggtg    900
```

```
gagcatgtgg tttaattcga agcaacgcga agaaccttac caggtcttga catcccaatg    960
accgtcctag agataggatt ttcccttcgg ggacattggt gacaggtggt gcatggttgt   1020
cgtcagctcg tgtcgtgaga tgttgggtta agtcccgcaa cgagcgcaac ccttattctt   1080
agttgccatc atttagttgg gcactctaag gagactgccg gtgacaaacc ggaggaaggt   1140
ggggatgacg tcaaatcatc atgccccttc tgacctgggc tacacacgtg ctacaatgga   1200
cgatacaaag agtcgcaaac tcgcgagggt aagctaatct cataaaatcg ttctcagttc   1260
ggattgtagg ctgcaactcg cctgcatgaa gccggaatcg ctagtaatcg cggatcagca   1320
tgccgcggtg aatacgttcc cgggccttgt acacaccgcc cgtcacacca cgagagtttg   1380
taacacccga agtcggtggg gtaaccgtaa ggagccagcc gctaagtgaa               1430
```

<210> SEQ ID NO 6
<211> LENGTH: 1432
<212> TYPE: DNA
<213> ORGANISM: Clostridium acidisoli

<400> SEQUENCE: 6

```
agagtttgat catggctcag gacgaacgct ggcggcgtgc ttaacacatg caagtcgagc     60
gagaaacctt cgggtttcta gcggcggacg ggtgagtaac acgtgggtaa cctgcctcaa    120
agtgggggat agccttccga aaggaagatt aataccgcat aacattgtag cttcgcatga    180
agcaacaatt aaaggagtaa tccgctttga gatggacccg cggcgcatta gctagttgga    240
gaggtaacgg ctcaccaagg cgacgatgcg tagccgacct gagagggtga tcggccacat    300
tggaactgag acacggtcca gactcctacg ggaggcagca gtgggaata ttgcacaatg    360 ggcgaaagcc tgatgcagca acgccgcgtg agtgatgaag gtcttcggat tgtaaagctc    420
tgtcttttgg gacgataatg acggtaccaa aggaggaagc cacggctaac tacgtgccag    480
cagccgcggt aatacgtagg tggcaagcgt tgtccggaat tactgggcgt aaaggatgtg    540
taggcggata tttaagtgag atgtgaaatc cccgagctca acttggggc tgcatttcaa    600 actgggtatc tagagtgcag gagaggaaag cggaattcct agtgtagcgg tgaaatgcgt    660
agagattagg aagaacatca gtggcgaagg cggctttctg gactgtaact gacgctgagg    720
catgaaagcg tggggagcaa acaggattag ataccctggt agtccacgcc gtaaacgatg    780
agtactaggt gtaggaggta tcgactcctt ctgtgccgca gttaacacaa taagtactcc    840
gcctgggaag tacggtcgca agattaaaac tcaaaggaat tgacggggc ccgcacaagc    900 agcggagcat gtggtttaat tcgaagcaac gcgaagaacc ttacctagac ttgacatccc    960
ctgaataacg tagagatacg cgaagccctt cggggcaggg agacaggtgg tgcatggttg   1020
tcgtcagctc gtgtcgtgag atgttgggtt aagtcccgca acgagcgcaa cccttatcat   1080
tagttgctac catttagttg agcactctag tgagactgcc cggttaacc gggaggaagg   1140 cggggatgac gtcaaatcat catgcccctt atgtctaggg ctacacacgt gctacaatgg   1200
tgagaacaac gagatgcaat accgcgaggt ggagcaaaac ttcaaaactc atctcagttc   1260
ggattgtagg ctgaaactcg cctacatgaa gttggagttg ctagtaatcg cgaatcagaa   1320
tgtcgcggtg aatacgttcc cgggccttgt acacaccgcc cgtcacacca tgagagctgg   1380
taacacccga agtccgtgag gtaaccttta ttggggccag cggccgaagg tg           1432
```

<210> SEQ ID NO 7
<211> LENGTH: 1438
<212> TYPE: DNA

<213> ORGANISM: Enterococcus faecium

<400> SEQUENCE: 7

| | | | | | |
|---|---|---|---|---|---|
| gcggctggct | ccaaaaggtt | acctcaccga | cttcgggtgt | acaaactct | cgtggtgtga | 60 |
| cgggcggtgt | gtacaaggcc | cgggaacgta | ttcaccgcgg | cgtgctgatc | cgcgattact | 120 |
| agcgattccg | gcttcatgca | ggcgagttgc | agcctgcaat | ccgaactgag | agaagcttta | 180 |
| agagattagc | ttagcctcgc | gacttcgcaa | ctcgttgtac | ttcccattgt | agcacgtgtg | 240 |
| tagcccaggt | cataaggggc | atgatgattt | gacgtcatcc | ccaccttcct | ccggtttgtc | 300 |
| accggcagtc | ttgctagagt | gcccaactga | atgatggcaa | ctaacaataa | gggttgcgct | 360 |
| cgttgcggga | cttaacccaa | catctcacga | cacgagctga | cgacaaccat | gcaccacctg | 420 |
| tcactttgcc | cccgaagggg | aagctctatc | tctagagtgg | tcaaaggatg | tcaagacctg | 480 |
| gtaaggttct | tcgcgttgct | tcgaattaaa | ccacatgctc | caccgcttgt | gcgggccccc | 540 |
| gtcaattcct | ttgagtttca | accttgcggt | cgtactcccc | aggcggagtg | cttaatgcgt | 600 |
| tagctgcagc | actgaagggc | ggaaaccctc | caacacttag | cactcatcgt | ttacggcgtg | 660 |
| gactaccagg | gtatctaatc | ctgtttgctc | cccacgcttt | cgagcctcag | cgtcagttac | 720 |
| agaccagaga | gccgccttcg | ccactggtgt | tcctccatat | atctacgcat | ttcaccgcta | 780 |
| cacatggaat | tccactctcc | tcttctgcac | tcaagtctcc | cagtttccaa | tgaccctccc | 840 |
| cggttgagcc | gggggctttc | acatcagact | taagaaaccg | cctgcgctcg | ctttacgccc | 900 |
| aataaatccg | gacaacgctt | gccacctacg | tattaccgcg | gctgctggca | cgtagttagc | 960 |
| cgtggctttc | tggttagata | ccgtcaaggg | atgaacagtt | actctcatcc | ttgttcttct | 1020 |
| ctaacaacag | agttttacga | tccgaaaacc | ttcttcactc | acgcggcgtt | gctcggtcag | 1080 |
| actttcgtcc | attgccgaag | attccctact | gctgcctccc | gtaggagttt | gggccgtgtc | 1140 |
| tcagtcccaa | tgtggccgat | caccctctca | ggtcggctat | gcatcgtggc | cttggtgagc | 1200 |
| cgttacctca | ccaactagct | aatgcaccgc | gggtccatcc | atcagcgaca | cccgaaagcg | 1260 |
| cctttcaaat | caaaaccatg | cggttttgat | tgttatacgg | tattagcacc | tgtttccaag | 1320 |
| tgttatcccc | ttctgatggg | caggttaccc | acgtgttact | cacccgttcg | ccactcctct | 1380 |
| ttttccggtg | gagcaagctc | cggtggaaaa | agaagcgtgc | gacttgcacg | tattaggc | 1438 |

<210> SEQ ID NO 8
<211> LENGTH: 1487
<212> TYPE: DNA
<213> ORGANISM: Enterococcus azikeevi

<400> SEQUENCE: 8

| | | | | | |
|---|---|---|---|---|---|
| agagtttgaa | tcatggctca | ggacgaacgc | tggcggcgtg | cctaatacat | gcaagtcgaa | 60 |
| cgcttctttt | tccaccggag | cttgctccac | cggaaaaaga | ggagtggcga | acgggtgagt | 120 |
| aacacgtggg | taacctgccc | atcagaaggg | gataacactt | ggaaacaggt | gctaataccg | 180 |
| tataacaatc | gaaaccgcat | ggttttgatt | tgaaaggcgc | tttcgggtgt | cgctgatgga | 240 |
| tggacccgcg | gtgcattagc | tagttggtga | ggtaacggct | caccaaggcg | acgatgcata | 300 |
| gccgacctga | gagggtgatc | ggccacattg | ggactgagac | acggcccaaa | ctcctacggg | 360 |
| aggcagcagt | agggaatctt | cggcaatgga | cgaaagtctg | accgagcaac | gccgcgtgag | 420 |
| tgaagaaggt | tttcggatcg | taaaactctg | ttgttagaga | agaacaagga | tgagagtaac | 480 |
| tgttcatccc | ttgacggtat | ctaaccagaa | agccacggct | aactacgtgc | cagcagccgc | 540 |
| ggtaatacgt | aggtggcaag | cgttgtccgg | atttattggg | cgtaaagcga | gcgcaggcgg | 600 |

```
tttcttaagt ctgatgtgaa agccccggc tcaaccgggg agggtcattg gaaactggga      660
gacttgagtg cagaagagga gagtggaatt ccatgtgtag cggtgaaatg cgtagatata      720
tggaggaaca ccagtggcga aggcggctct ctggtctgta actgacgctg aggctcgaaa      780
gcgtggggag caaacaggat tagataccct ggtagtccac gccgtaaacg atgagtgcta      840
agtgttggag ggtttccgcc cttcagtgct gcagctaacg cattaagcac tccgcctggg      900
gagtacgacc gcaaggttga aactcaaagg aattgacggg ggcccgcaca agcggtggag      960
catgtggttt aattcgaagc aacgcgaaga accttaccag gtcttgacat cctttgacca     1020
ctctagagat agagcttccc cttcggggc aaagtgacag gtggtgcatg gttgtcgtca     1080
gctcgtgtcg tgagatgttg ggttaagtcc cgcaacgagc gcaacccta ttgttagttg     1140
ccatcattta gttgggcact ctagcaagac tgccggtgac aaaccggagg aaggtgggga     1200
tgacgtcaaa tcatcatgcc ccttatgacc tgggctacac acgtgctaca atgggaagta     1260
caacgagtcg caaagtcgcg aggctaagct aatctcttaa agcttctctc agttcggatt     1320
gtaggctgca actcgcctac atgaagccgg aatcgctagt aatcgcggat cagcacgccg     1380
cggtgaatac gttcccgggc cttgtacaca ccgcccgtca caccacgaga gtttgtaaca     1440
cccgaagtcg gtgaggtaac cttttggagc cagccgccta aggtgat                  1487

<210> SEQ ID NO 9
<211> LENGTH: 1429
<212> TYPE: DNA
<213> ORGANISM: Enterobacter roggenkampii

<400> SEQUENCE: 9
gcagctacac atgcaagtcg agcggcagcg aagtagctt gctactttgc cggcgagcgg       60
cggacgggtg agtaatgtct gggaaactgc ctgatggagg gggataacta ctggaaacgg      120
tagctaatac cgcataacgt cgcaagacca agagggggga ccttcgggcc tcttgccatc      180
agatgtgccc agatgggatt agctagtagg tggggtaacg gctcacctag gcgacgatcc      240
ctagctggtc tgagaggatg accagccaca ctggaactga gacacggtcc agactcctac      300
gggaggcagc agtggggaat attgcacaat gggcgcaagc ctgatgcagc catgccgcgt      360
gtatgaagaa ggccttcggg ttgtaaagta ctttcagcgg ggaggaaggc gttgaggtta      420
ataacctcag cgattgacgt tacccgcaga agaagcaccg gctaactccg tgccagcagc      480
cgcggtaata cggagggtgc aagcgttaat cggaattact gggcgtaaag cgcacgcagg      540
cggtctgtca agtcggatgt gaaatccccg ggctcaacct gggaactgca ttcgaaactg      600
gcaggctaga gtcttgtaga gggggtaga attccaggtg tagcggtgaa atgcgtagag      660
atctggagga ataccggtgg cgaaggcggc ccctggaca aagactgacg ctcaggtgcg      720
aaagcgtggg gagcaaacag gattagatac cctggtagtc cacgccgtaa acgatgtcga      780
cttggaggtt gtgcccttga ggcgtggctt ccggagctaa cgcgttaagt cgaccgcctg      840
gggagtacgg ccgcaaggtt aaaactcaaa tgaattgacg ggggcccgca caagcggtgg      900
agcatgtggt ttaattcgat gcaacgcgaa gaaccttacc tactcttgac atccagagaa      960
cttagcagag atgctttggt gccttcggga actctgagac aggtgctgca tggctgtcgt     1020
cagctcgtgt tgtgaaatgt tgggttaagt cccgcaacga gcgcaaccct tatcctttgt     1080
tgccagcggt ccgccggga actcaaagga gactgccagt gataaactgg aggaaggtgg     1140
ggatgacgtc aagtcatcat ggcccttacg agtagggcta cacacgtgct acaatggcgc     1200
```

```
atacaaagag aagcgacctc gcgagagcaa gcggacctca taaagtgcgt cgtagtccgg    1260
attggagtct gcaactcgac tccatgaagt cggaatcgct agtaatcgta gatcagaatg    1320
ctacggtgaa tacgttcccg ggccttgtac acaccgcccg tcacaccatg ggagtgggtt    1380
gcaaaagaag taggtagctt aaccttcggg agggcgctac cacttgatt                1429

<210> SEQ ID NO 10
<211> LENGTH: 1401
<212> TYPE: DNA
<213> ORGANISM: Clostridium kogasensis

<400> SEQUENCE: 10
cggcagctac acatgcaagt cgagcgatga atcccttcg gggatggatt agcggcggac      60
gggtgagtaa cacgtgggca acctgcctca aagtggggga tagcctcccg aaagggagat   120
taataccgca taatgttaga tcttcacatg aagaactaat taaaggagca atccgctttg   180
agatgggccc gcggcgcatt agctagttgg tgaggtaatg gctcaccaag gcgacgatgc   240
gtagccgacc tgagagggtg atcggccaca ttggaactga gacacggtcc agactcctac   300
gggaggcagc agtggggaat attgcacaat gggggaaacc ctgatgcagc aacgccgcgt   360
gagtgatgaa ggtcttcgga ttgtaaagct ctgtcttttg gacgataat gacggtacca   420 aaggaggaag ccacggctaa ctacgtgcca gcagccgcgg taatacgtag gtggcgagcg   480
ttgtccggat ttactgggcg taaagggtgc gtaggcggat atttaagtgg gatgtgaaat   540
acccgggctc aacttgggtg ctgcattcca aactggatat ctagagtgcg ggagaggaga   600
gtggaattcc tagtgtagcg gtgaaatgcg tagagattag gaagaacacc agtggcgaag   660
gcgactctct ggaccgtaac tgacgctgag gcacgaaagc gtgggagca aacaggatta   720 gataccctgg tagtccacgc cgtaaacgat gaatactagg tgtaggaggt atcgacccct   780
tctgtgccgc agttaacaca ataagtattc cgcctgggga gtacggtcgc aagattaaaa   840
ctcaaaggaa ttgacgggg cccgcacaag cagcggagca tgtggtttaa ttcgaagcaa   900
cgcgaagaac cttacctaga cttgacatac cctgaattac cggtaatgcg ggaagccctt   960
cggggcaggt atacaggtgg tgcatggttg tcgtcagctc gtgtcgtgag atgttaggtt  1020
aagtcctgca acgagcgcaa cccctattat tagttgctac cattaagttg agcactctag  1080
taagactgcc tgggttaacc aggaggaagg cgggatgac gtcaaatcat catgccctt   1140 atgtctaggg ctacacacgt gctacaatgg gcggtacaaa aagatgcaaa ctcgcgagag  1200
tgagccaaac tttaaaaccg cccccagttc ggattgtagg ctgaaactcg cctacatgaa  1260
gccggagttg ctagtaatcg cgaatcagca tgtcgcggtg aatacgttcc cgggccttgt  1320
acacaccgcc cgtcacacca tgagagctgg caacacccga agtccgtgag gtaaccgtaa  1380
ggagccagcg gccgaagtgg g                                             1401
```

MICROBIOLOGICAL TREATMENT SYSTEM FOR ETHYLENE OXIDE EXHAUST GAS

CROSS-REFERENCE TO RELATED PATENT APPLICATIONS

This application is a Bypass Continuation of PCT/CN2020/101142, filed Jul. 9, 2020, which application claims the benefit of Chinese Patent Application No. CN202020340594.1 filed on 18 Mar. 2020, Chinese Patent Application No. CN202010190370.1 filed on 18 Mar. 2020, Chinese Patent Application No. CN202020348776.3 filed on 18 Mar. 2020 and Chinese Patent Application No. CN202010194457.6 filed on 18 Mar. 2020, the entire content of which is incorporated herein by reference in its entirety for all purposes.

TECHNICAL FIELD

The present disclosure relates to the field of microbiological technology, and more particularly, to a microbiological treatment system for treatment of ethylene oxide exhaust gas.

SEQUENCE STATEMENT

Incorporated by reference herein in its entirety is the Sequence Listing entitled "1211_CK12_ST25_WO" created Jun. 2, 2020, size of 19.6 kilobytes.

BACKGROUND

Currently, ethylene oxide gas sterilization is the most widely used method in the field of low temperature sterilization. Ethylene oxide can be widely used for sterilization of electronic instruments, chemical instruments, paper products, chemical fiber products, plastics products, ceramics, and metal products, due to its high efficiency, low cost, strong penetration through complex items, wide matching sterilization items, and minimal damage to instruments.

However, since ethylene oxide has very active chemical properties, and is flammable, explosive, and highly toxic, direct discharge may cause severe pollution to the environment and may be a great biological hazard. Hence, there is a need for harmless disposal of ethylene oxide exhaust gas. For example, at present, after sterilization with ethylene oxide gas, the ethylene oxide exhaust gas in the sterilizer is generally treated in one of the following two ways: (a) catalytic combustion, in which the sterilization exhaust gas is directly catalytically combusted, which method may cause a potential safety hazard due to the flammability and explosibility of the ethylene oxide; and (b) absorption process, in which ethylene glycol is formed by acid absorption, which method can only be used to treat high concentration ethylene oxide exhaust gases, and the acid may cause secondary pollution. Although the foregoing methods can reduce the environmental hazards caused by ethylene oxide, improper handling may cause secondary pollution and safety hazards, and may lead to waste of resources.

In addition, there are few reports on methods for recovering ethylene oxide exhaust gas. Data shows that ethylene oxide was recovered by condensation at −29° C., but such method results in high energy consumption equipment with lower yield since ethylene oxide is quite difficult to separate from water.

Therefore, it is an urgent technical problem to be solved for those skilled in the art to provide a safe and effective method for the treatment of ethylene oxide exhaust gas.

Hence, there may be a need for more robust and scalable solutions for implementing sterilization technologies, and, more particularly, for implementing a microbiological treatment system for treatment of ethylene oxide exhaust gas.

SUMMARY

The present disclosure provides a microbiological treatment system for treatment of ethylene oxide exhaust gas, which enables safe and efficient treatment for ethylene oxide exhaust gas, for example, sterilization exhaust gas, in particular, exhaust gas resulting from sterilization of medical devices or the like.

In an aspect of the present disclosure, there may be provided a microbiological treatment system for treatment of ethylene oxide exhaust gas including a hydration system and at least two microbiological degradation systems. The hydration system may include a gas-liquid mixing chamber, a first gas inlet, a first gas outlet, a first liquid inlet, and a first liquid outlet. The first gas inlet, the first gas outlet, the first liquid inlet, and the first liquid outlet may be in fluid communication with the gas-liquid mixing chamber. The first gas inlet may be configured to introduce an ethylene oxide exhaust gas into the gas-liquid mixing chamber to mix with an aqueous solution (e.g., water, or the like) to form an ethylene oxide exhaust liquor, and the first liquid outlet may be configured to discharge the ethylene oxide exhaust liquor. Each of the microbiological degradation systems may include a degradation chamber containing degradation bacteria that may be selected from any one of anaerobic bacteria, facultative bacteria, and aerobic bacteria. The degradation chambers of the at least two microbiological degradation systems may be in fluid communication sequentially in a predetermined degradation sequence. A degradation chamber that is located most upstream in the degradation sequence might have a liquid inlet that may be in fluid communication with the first liquid outlet of the hydration system.

In an embodiment, the at least two microbiological degradation systems may include a first microbiological degradation system, a second microbiological degradation system, and a third microbiological degradation system. A degradation chamber of the first microbiological degradation system may be located most upstream in the degradation sequence and may contain anaerobic bacteria, while a degradation chamber of the second microbiological degradation system may be located at a position that is downstream of the degradation chamber of the first microbiological degradation system and may contain facultative bacteria, and a degradation chamber of the third microbiological degradation system may be located at a position that is downstream of the degradation chamber of the second microbiological degradation system and may contain aerobic bacteria. In an embodiment, the degradation chamber of the third microbiological degradation system may have a second gas inlet and a second gas outlet, and the first gas outlet may be in fluid communication with the second gas inlet via a first pipe.

In an embodiment, the anaerobic bacteria may include any one or more microorganisms selected from the group consisting of *Klebsiella pneumoniae*, *Clostridium faecalis*, *Clostridium kogasensis*, *Clostridium acidisoli*, *Enterobacteriaceae*, and *Photosynthetic* bacteria. According to some embodiments, the facultative bacteria may include any one or more microorganisms selected from the group consisting of *Kurthia gibsonii*, *Lactobacillus*, *Enterococcus faecalis*, *Alcaligenes*, *Morganella morganii*, and *Enterococcus*. According to some embodiments, the aerobic bacteria may include any one or more microorganisms selected from the group consisting of *Acetobacter peroxydans*, *Escherichia coli*, *Cycloclasticus*, *Bacillus*, and *Pseudomonas aeruginosa*.

In some embodiments, the *Acetobacter peroxydans* bacteria might comprise *Acetobacter peroxydans* strain EO-01 with the Deposit Number of CGMCC No. 18431 or an *Acetobacter peroxydans* strain comprising the 16S rDNA sequence of SEQ ID NO: 2.

In some embodiments, the *Lactobacillus* bacteria might comprise *Lactobacillus fermentum* strain EO-02 with the Deposit Number of CGMCC No. 18432 or a *Lactobacillus fermentum* strain comprising the 16S rDNA sequence of SEQ ID NO: 3.

In some embodiments, the *Bacillus* bacteria might comprise *Bacillus subtilis* strain EO-03 with the Deposit Number of CGMCC No. 18433 or a *Bacillus subtilis* strain comprising the 16S rDNA sequence of SEQ ID NO: 4.

In some embodiments, the *Enterococcus* bacteria might comprise *Enterococcus faecium* strain EO-04 with the Deposit Number of CGMCC No. 18434 or an *Enterococcus faecium* strain comprising the 16S rDNA sequence of SEQ ID NO: 7.

In some embodiments, the *Alcaligenes* bacteria might comprise *Alcaligenes faecalis* strain EO-05 with the Deposit Number of CGMCC No. 18435 or an *Alcaligenes faecalis* strain comprising the 16S rDNA sequence of SEQ ID NO: 1.

In some embodiments, the *Kurthia gibsonii* bacteria might comprise *Kurthia gibsonii* strain EO-06 with the Deposit Number of CGMCC No. 18436 or a *Kurthia gibsonii* strain comprising the 16S rDNA sequence of SEQ ID NO: 5.

In some embodiments, the *Enterococcus* bacteria might comprise *Enterococcus azikeevi* strain EO-07 with the Deposit Number of CGMCC No. 18437 or an *Enterococcus azikeevi* strain comprising the 16S rDNA sequence of SEQ ID NO: 8.

In some embodiments, the *Clostridium* bacteria might comprise *Clostridium kogasensis* strain EO-08 with the Deposit Number of CGMCC No. 18438 or a *Clostridium kogasensis* strain comprising the 16S rDNA sequence of SEQ ID NO: 10.

In some embodiments, the *Clostridium* bacteria might comprise *Clostridium acidisoli* strain EO-09 with the Deposit Number of CGMCC No. 18439 or a *Clostridium acidisoli* strain comprising the 16S rDNA sequence of SEQ ID NO: 6.

In some embodiments, the *Enterobacteriaceae* bacteria might comprise *Enterobacter roggenkampii* strain EO-10 with the Deposit Number of CGMCC No. 18440 or an *Enterobacter roggenkampii* strain comprising the 16S rDNA sequence of SEQ ID NO: 9.

The foregoing strains were deposited at China General Microbiological Culture Collection Center, with the deposit address being Institute of Microbiology of Chinese Academy of Sciences, NO. 1 West Beichen Road, Beijing 100101, China.

In an embodiment, the anaerobic bacteria, the facultative bacteria, and the aerobic bacteria may be ethylene oxide dominant degradation strains that may be screened, induced, and acclimated with ethylene oxide.

In an embodiment, the microbiological treatment system may further include a recovery system that may be in fluid communication with a liquid outlet of the degradation chamber that is located most downstream in the degradation sequence. In an embodiment, the recovery system may include a clarification tank and a liquid storage tank. The clarification tank may include a liquid inlet that may be in fluid communication with the liquid outlet of the degradation chamber that is located most downstream in the degradation sequence via a second pipe, and a liquid outlet that may be in fluid communication with the liquid storage tank via a third pipe. The hydration system may be in fluid communication with the liquid storage tank through the first liquid inlet. In an embodiment, the clarification tank may include a sludge outlet that may be in fluid communication with a liquid inlet of the degradation chamber that is located most upstream in the degradation sequence via a sludge pipe.

In an embodiment, the microbiological treatment system may further include a buffer tank including a second liquid inlet and a second liquid outlet. The first liquid outlet may be in fluid communication with the second liquid inlet, and the second liquid outlet may be in fluid communication with the liquid inlet of the degradation chamber that is located most upstream in the degradation sequence.

In an embodiment, the microbiological treatment system may further include an ethylene oxide adsorption system including a gas passage, a third gas inlet, and a third gas outlet. The third gas inlet and the third gas outlet may be in fluid communication with the gas passage. An adsorbent material may be provided in the gas passage. The third gas inlet may be configured to introduce ethylene oxide exhaust gas, and may be in fluid communication with the first gas inlet. In an embodiment, the adsorbent material may include any one or more materials selected from the group consisting of a coconut shell activated carbon, a columnar activated carbon, and an activated carbon fiber. In an embodiment, the ethylene oxide adsorption system may further include an interlayer surrounding the gas passage, a hot water inlet pipe, a hot water outlet pipe, a cold water inlet pipe, a cold water outlet pipe, and a gas recovery pipe. The hot water inlet pipe, the hot water outlet pipe, the cold water inlet pipe, and the cold water outlet pipe may be in fluid communication with the interlayer, while the gas recovery pipe may be in fluid communication with the gas passage.

In an embodiment, the hydration system may further include: a tower body including the gas-liquid mixing chamber, the first gas inlet and the first liquid outlet being located at a lower portion of the tower body, and the first gas outlet and the first liquid inlet being located at an upper portion of the tower body; a gas inlet pipe connected at the first gas inlet, a portion of the gas inlet pipe extending into the gas-liquid mixing chamber, with the portion of the gas inlet pipe that is located in the gas-liquid mixing chamber being provided with a plurality of gas spraying holes; and a liquid inlet pipe connected at the first liquid inlet, a portion of the liquid inlet pipe extending into the gas-liquid mixing chamber, with the portion of the liquid inlet pipe that is located in the gas-liquid mixing chamber being provided with a plurality of liquid spraying holes.

In an embodiment, the hydration system may further include a water baffle disposed in the gas-liquid mixing chamber, an edge of the water baffle being connected to a wall of the gas-liquid mixing chamber. The water baffle may be located between the liquid inlet pipe and the first gas outlet, and the water baffle may be provided with an air hole. In an embodiment, the hydration system may further include a gas guide plate disposed in the gas-liquid mixing chamber, an edge of the gas guide plate being connected to the wall of the gas-liquid mixing chamber. The gas guide plate may be located between the first gas outlet and the water baffle, and the gas guide plate may be provided with a gas guiding hole. In an embodiment, both of the water baffle and the gas guide plate may be funnel-shaped.

In an embodiment, the hydration system may further include a circulation pipeline located outside the tower body and a pump mounted on the circulation pipeline. An inlet of the circulation pipeline may be in fluid communication with the first liquid outlet, and an outlet of the circulation pipeline may extend into the gas-liquid mixing chamber and may be in fluid communication with the liquid inlet pipe.

In an another aspect of the present disclosure, there may be provided a water adsorption microbiological treatment system for treatment of ethylene oxide sterilization gas, including an ethylene oxide sterilization exhaust gas pipe, a hydration system, a buffer tank, a first microbiological degradation system, a second microbiological degradation system, a third microbiological degradation system, a clarification tank, a sludge pipe, a liquid storage tank, and a gas outlet pipe. The hydration system, the buffer tank, the first microbiological degradation system, the second microbiological degradation system, the third microbiological degradation system, the clarification tank, and the liquid storage tank may be sequentially fluidly connected via at least one pipe, and the hydration system may be fluidly connected to the liquid storage tank. The ethylene oxide sterilization exhaust gas pipe may be fluidly connected to the hydration system, and the hydration system may be fluidly connected to the third microbiological degradation system via the gas outlet pipe. The sludge pipe may be disposed between the buffer tank and the first microbiological degradation system and may be fluidly connected to the clarification tank.

These and other objects, advantages, purposes, and features will become apparent upon review of the following detailed description in conjunction with the drawings.

BRIEF DESCRIPTION OF THE DRAWINGS

A further understanding of the nature and advantages of particular embodiments may be realized by reference to the remaining portions of the specification and the drawings, in which like reference numerals are used to refer to similar components. In some instances, a sub-label is associated with a reference numeral to denote one of multiple similar components. When reference is made to a reference numeral without specification to an existing sub-label, it is intended to refer to all such multiple similar components.

DETAILED DESCRIPTION OF THE EMBODIMENTS

Figure 1:
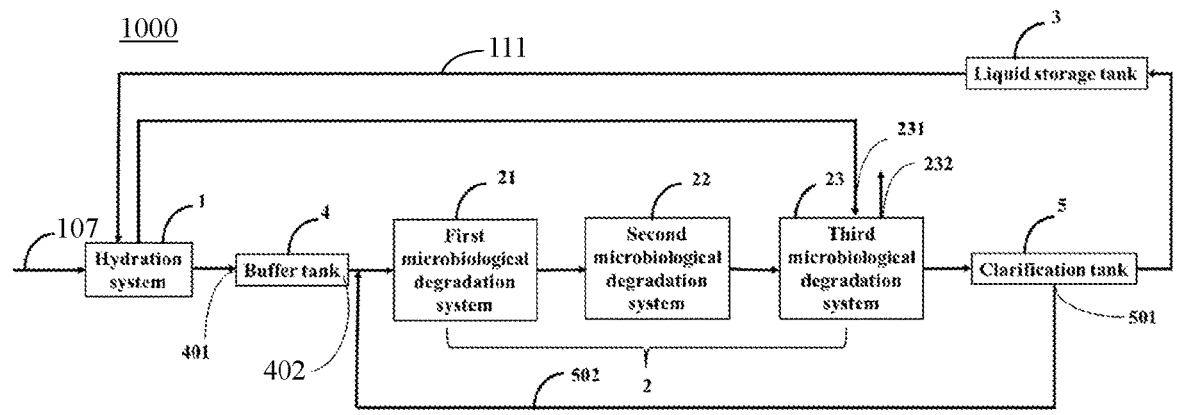
FIG. 1 is a schematic diagram depicting a microbiological treatment system according to one embodiment of the present disclosure.

Exemplary embodiments will be described hereafter with reference to the drawings to clearly and fully illustrate the technical solutions of the present disclosure. All other embodiments obtained by a person of ordinary skill in the art based on the embodiments in the present disclosure without creative efforts are within the scope of the present disclosure.

The following detailed description illustrates a few exemplary embodiments in further detail to enable one of skill in the art to practice such embodiments. The described examples are provided for illustrative purposes and are not intended to limit the scope of the disclosure.

In the following description, for the purposes of explanation, numerous specific details are set forth in order to provide a thorough understanding of the described embodiments. It will be apparent to one skilled in the art, however, that other embodiments of the present disclosure may be practiced without some of these specific details. In other instances, certain structures and devices are shown in block diagram form. Several embodiments are described herein, and while various features are ascribed to different embodiments, it should be appreciated that the features described with respect to one embodiment may be incorporated with other embodiments as well. By the same token, however, no single feature or features of any described embodiment should be considered essential to every embodiment of the disclosure, as other embodiments of the disclosure may omit such features.

Unless otherwise indicated, all numbers used herein to express quantities, dimensions, and so forth used should be understood as being modified in all instances by the term "about." In this application, the use of the singular includes the plural unless specifically stated otherwise, and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

The microbiological treatment system according to the present disclosure may include a hydration system and at least two microbiological degradation systems. The hydration system may include a gas-liquid mixing chamber, a first gas inlet, a first gas outlet, a first liquid inlet, and a first liquid outlet. The first gas inlet, the first gas outlet, the first liquid inlet, and the first liquid outlet may be in fluid communication with the gas-liquid mixing chamber. The first gas inlet may be configured to introduce an ethylene oxide exhaust gas into the gas-liquid mixing chamber to mix with an aqueous solution (e.g., water, or the like) to form an ethylene oxide exhaust liquor, and the first liquid outlet may be configured to discharge the ethylene oxide exhaust liquor. Each of the microbiological degradation systems may include a degradation chamber containing degradation bacteria that may be selected from any one of anaerobic bacteria, facultative bacteria, and aerobic bacteria. The degradation chambers of the at least two microbiological degradation systems may be in fluid communication sequentially in a predetermined degradation sequence. A degradation chamber that is located most upstream in the degradation sequence might have a liquid inlet that may be in fluid communication with the first liquid outlet of the hydration system.

According to an embodiment of the microbiological treatment system provided above, the ethylene oxide exhaust gas might enter the microbiological treatment system, and may be mixed with an aqueous solution capable of absorbing ethylene oxide, such as water, in the hydration system. The obtained exhaust water might enter the second or third microbiological degradation system via a pipe, may be degraded as a carbon source by the microorganisms in the microbiological degradation systems. Eventually, a gas without contamination, or with very little contamination, may be discharged to the atmosphere, thereby realizing a safe and effective treatment for the ethylene oxide in the ethylene oxide exhaust gas.

FIG. 1 shows a schematic diagram of a microbiological treatment system 1000 according to an embodiment of the present disclosure.

The microbiological treatment system 1000 according to one embodiment of the present disclosure may include a hydration system 1, one or more microbiological degradation systems 2, and a liquid storage tank 3. The hydration system 1 may be fluidly connected to the one or more microbiological degradation systems 2 via a pipe(s).

Figure 3:
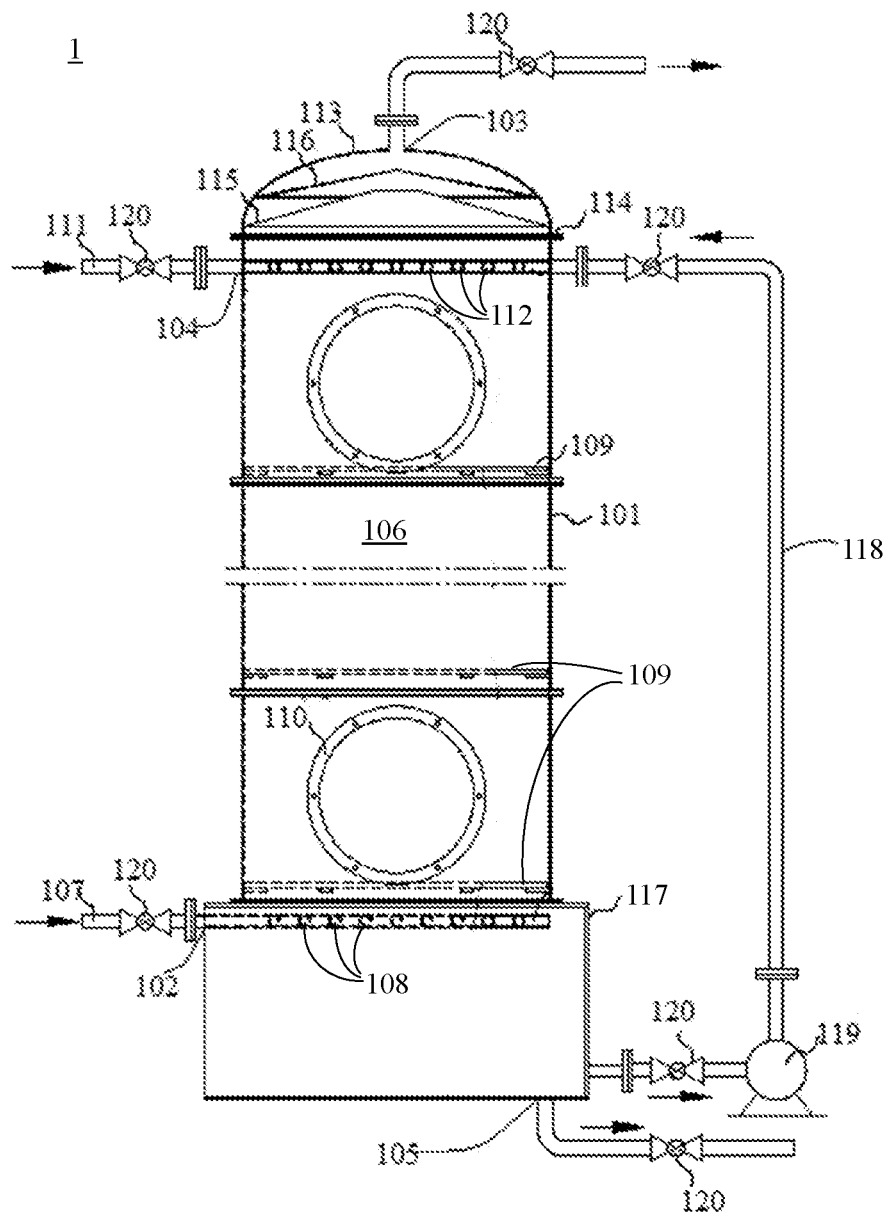
FIG. 3 is a schematic diagram depicting a hydration system according to one embodiment of the present disclosure.

As shown in FIG. 3, the hydration system 1 may include a tower body 101. The tower body 101 may have various shapes, for example, a hollow cylindrical shape, or the like. A first gas inlet 102 and a first liquid outlet 105 may be formed at a lower portion of the tower body 101, while a first liquid inlet 104 and a first gas outlet 103 may be formed at an upper portion of the tower body 101. A gas-liquid mixing chamber 106 may be formed inside the tower body 101, and each of the first gas inlet 102, the first gas outlet 103, the first liquid inlet 104, and the first liquid outlet 105 may be in fluid communication with the gas-liquid mixing chamber 106.

The hydration system 1 may further include a gas inlet pipe 107 connected at the first gas inlet 102. A portion of the gas inlet pipe 107 may extend into the gas-liquid mixing chamber 106, with the portion of the gas inlet pipe 107 that is located in the gas-liquid mixing chamber 106 being provided with a plurality of gas spraying holes 108. The ethylene oxide exhaust gas may be introduced via the gas inlet pipe 107 and may be dispersed in the gas-liquid mixing chamber 106 via the gas spraying holes 108.

The interior of the tower body 101 may be provided with one or more gas dispersers 109 that may have various forms capable of dispersing gas and may be located above the gas spraying holes 108. The gas dispersers 109 serve to re-disperse the ethylene oxide sterilization exhaust gas that may be injected from the gas inlet pipe 107 into the gas-liquid mixing chamber 106 and dispersed through the gas spraying holes 108, so that the ethylene oxide sterilization exhaust gas can be more evenly dispersed within or throughout the gas-liquid mixing chamber 106. The gas disperser 109 may be detachably connected to the interior of the tower body 101. Further, referring to FIG. 3, three gas dispersers 109 are shown, that is, a first gas disperser, a second gas disperser, and a third gas disperser. The first gas disperser, the second gas disperser, and the third gas disperser may be spaced apart from each other within the tower body 101 so as to perform a multistage dispersion of the ethylene oxide sterilization exhaust gas. In addition, the tower body 101 may have a suitable height as appropriate, and may have an appropriate number of gas dispersers 109 as required, to enhance absorption of the ethylene oxide sterilization exhaust gas by water that is contained in the tower body 101.

The hydration system 1 may further include at least one viewing hole 110 that may each be in the form of a transparent window, or the like, and that may each be detachably disposed on the wall of the tower body 101, for example, to allow an operator to watch the interior of the tower body 101 or to replace and maintain internal components, such as to replace or maintain the gas disperser(s) 109, or the like. In some implementations, the at least one viewing hole 110 may be detachably connected to the tower body 101, at the wall of the tower body 101. The at least one viewing hole 110 may include a first viewing hole and a second viewing hole. The first viewing hole may be formed in the wall of the tower body 101 at a height below the first liquid inlet 104, while the second viewing hole may be formed in the wall of the tower body 101 at a height above the first gas inlet 102.

The hydration system 1 may further include a liquid inlet pipe 111 that may be connected at the first liquid inlet 104. A portion of the liquid inlet pipe 111 may extend into the gas-liquid mixing chamber 106. The portion of the liquid inlet pipe 111 that may be extended inside the gas-liquid mixing chamber 106 may be provided with a plurality of liquid spraying holes 112.

The liquid storage tank 3 (as shown in FIG. 1) may contain an aqueous solution capable of absorbing ethylene oxide, such as water, or the like. Water (or other suitable aqueous solution or liquid) may be introduced from the liquid storage tank 3 through the liquid inlet pipe 111 into the hydration system 1, and may be dispersed in the gas-liquid mixing chamber 106 through the liquid spraying holes 112 in the liquid inlet pipe 111, forming descending liquid mists and/or droplets (in this case, water mists and/or water droplets). The descending liquid mists and/or droplets may meet the ascending ethylene oxide exhaust gas that may be sprayed from the gas spraying holes 108 in the gas inlet pipe 107. As the descending liquid mists and/or droplets meet the ascending ethylene oxide exhaust gas, the ethylene oxide in the ethylene oxide exhaust gas may be absorbed by the liquid (e.g., water, or the like), thereby forming an ethylene oxide exhaust liquor. The ethylene oxide exhaust liquor may fall into a bottom portion of the tower body 101.

The tower body 101 may be integrally formed with, or may include, an upper cover 113 at the top portion thereof. The upper cover 113 may, for example, sealingly engage with the remaining portion(s) of the tower body 101 by use of a sealing gasket 114 to close the gas-liquid mixing chamber 106. The first gas outlet 103 may be provided on a top portion of the upper cover 113.

The hydration system 1 may further include a water baffle 115 that is disposed below the upper cover 113. The water baffle 115 may be disposed in the gas-liquid mixing chamber 106, with an edge of the water baffle 115 being connected to the wall of the gas-liquid mixing chamber 106 (not shown in FIG. 3; e.g., in the case that the upper cover 113 is integrally formed with the tower body 101, or the like) or to a wall of the upper cover 113 (as shown in FIG. 3). In some embodiments, the water baffle 115 may be funnel-shaped, may be located between the liquid inlet pipe 111 and the first gas outlet 103, and may have an air hole for retaining water and for allowing gas to pass.

The hydration system 1 may further include a gas guide plate 116 that may be provided in the gas-liquid mixing chamber 106 between the first gas outlet 103 and the water baffle 115, and an edge of the gas guide plate 116 may be connected to the wall of the gas-liquid mixing chamber 106 (not shown in FIG. 3; e.g., in the case that the upper cover 113 is integrally formed with the tower body 101, or the like) or to the wall of the upper cover 113 (as shown in FIG. 3). In some embodiments, the gas guide plate 116 may be funnel-shaped, and may have a gas guiding hole leading to the first gas outlet 103. A residual gas resulting from the liquid (e.g., water, or the like) absorbing the ethylene oxide in the ethylene oxide exhaust gas may pass through the water baffle 115, where the liquid (e.g., water, or the like) in the residual gas may be retained. The residual gas may then pass through the first gas outlet 103 via the gas guiding hole, and may be discharged through a pipe into the downstream microbiological degradation system or may be directly discharged into the external environment.

A liquid storage chamber 117 may be included in the tower body 101 at the lower portion to collect ethylene oxide exhaust liquor. The bottom portion of the liquid storage chamber 117 may be provided with the first liquid outlet 105 to discharge the ethylene oxide exhaust liquor.

The hydration system 1 may further include a circulation pipeline 118 that is located outside the tower body 101 and a pump 119 that is mounted on the circulation pipeline 118. The circulation pipeline 118 may include an inlet that may be in fluid communication with the first liquid outlet 105 and/or with the liquid storage chamber 117 at a height higher than the first liquid outlet 105. The circulation pipeline 118 may further include an outlet that may extend into the gas-liquid mixing chamber 106, and that may be in fluid communication with the liquid inlet pipe 111.

According to some embodiments, the hydration system 1 may be provided with six valves 120. The valves 120 may each be provided in one of: (i) the liquid inlet pipe 111 between the first liquid inlet 104 and the liquid storage tank 3; (ii) the pipe between the first gas outlet 103 and the microbiological degradation system 2; (iii) the portion of the circulation pipeline 118 between the pump 119 and the liquid inlet pipe 111; (iv) the portion of the gas inlet pipe 107 outside the hydration system 2; (v) the pipe between the first liquid outlet 105 and the downstream microbiological degradation system 2; and (vi) the portion of the circulation pipeline 118 between the first liquid outlet 105 or the liquid storage chamber 117 and the pump 119. By using such valves 120, each operational step in the hydration process of the ethylene oxide exhaust gas and the aqueous solution occurring in the hydration system 1 can be controlled by an automatic control system, thus realizing full automatic control, and, consequently, simple, convenient, and fast operation. Meanwhile, the flow of the gas or liquid from or out of the hydration system 1, or the circulation of the gas or liquid in the hydration system 1, can be automatically carried out separately or simultaneously.

We now turn back to the non-limiting embodiment of FIG. 1. In some embodiments, the microbiological treatment system 1000 may include a buffer tank 4 including a second liquid inlet 401, the second liquid inlet 401 being in fluid communication with the first liquid outlet 105 via a pipe to introduce ethylene oxide exhaust liquor into the buffer tank 4. The buffer tank 4 may further include a second liquid outlet 402, the second liquid outlet 402 being in fluid communication with a liquid inlet of the most upstream degradation chamber of the one or more microbiological degradation systems 2 via a pipe. For example, as shown in FIG. 1, the second liquid outlet 402 of the buffer tank 4 may be in fluid communication with the liquid inlet of a first microbiological degradation system 21, which will be described below.

As shown in FIG. 1, the one or more microbiological degradation systems 2 of the microbiological treatment system 1000 may include three microbiological degradation systems 2 connected in sequence by a pipe. For example, the one or more microbiological degradation systems 2 may include a first microbiological degradation system 21, a second microbiological degradation system 22, and a third microbiological degradation system 23. Each of the microbiological degradation systems may include a degradation chamber.

The degradation chamber of the first microbiological degradation system 21 may be located most upstream in the degradation sequence, and may contain anaerobic bacteria that may include any one or more microorganisms selected from the group consisting of *Klebsiella pneumoniae*, *Clostridium faecalis*, *Clostridium kogasensis*, *Clostridium acidisoli*, *Enterobacteriaceae*, and *Photosynthetic* bacteria. The anaerobic bacteria in the degradation chamber of the first microbiological degradation system 21 can grow under anaerobic conditions using ethylene oxide as a carbon source, thereby degrading ethylene oxide in the ethylene oxide exhaust liquor to obtain a primary degradation exhaust liquor.

In some embodiments, the *Clostridium* bacteria might comprise *Clostridium kogasensis* strain EO-08 with the Deposit Number of CGMCC No. 18438 or a *Clostridium kogasensis* strain comprising the 16S rDNA sequence of SEQ ID NO: 10.

In some embodiments, the *Clostridium* bacteria might comprise *Clostridium acidisoli* strain EO-09 with the Deposit Number of CGMCC No. 18439 or a *Clostridium acidisoli* strain comprising the 16S rDNA sequence of SEQ ID NO: 6.

In some embodiments, the *Enterobacteriaceae* bacteria might comprise *Enterobacter roggenkampii* strain EO-10 with the Deposit Number of CGMCC No. 18440 or an *Enterobacter roggenkampii* strain comprising the 16S rDNA sequence of SEQ ID NO: 9.

The degradation chamber of the second microbiological degradation system 22 may be located downstream of the degradation chamber of the first microbiological degradation system 21, and may contain facultative bacteria that may include any one or more microorganisms selected from the group consisting of *Kurthia gibsonii*, *Lactobacillus*, *Enterococcus faecalis*, *Alcaligenes*, *Morganella morganii*, and *Enterococcus*. The facultative bacteria in the degradation chamber of the second microbiological degradation system 22 can grow under hypoxic conditions using ethylene oxide as a carbon source, thereby degrading the ethylene oxide remaining in the primary degradation exhaust liquor to obtain a secondary degradation exhaust liquor.

In some embodiments, the *Kurthia gibsonii* bacteria might comprise *Kurthia gibsonii* strain EO-06 with the Deposit Number of CGMCC No. 18436 or a *Kurthia gibsonii* strain comprising the 16S rDNA sequence of SEQ ID NO: 5.

In some embodiments, the *Lactobacillus* bacteria might comprise *Lactobacillus fermentum* strain EO-02 with the Deposit Number of CGMCC No. 18432 or a *Lactobacillus fermentum* strain comprising the 16S rDNA sequence of SEQ ID NO: 3.

In some embodiments, the *Enterococcus* bacteria might comprise *Enterococcus faecium* strain EO-04 with the Deposit Number of CGMCC No. 18434 or an *Enterococcus faecium* strain comprising the 16S rDNA sequence of SEQ ID NO: 7.

In some embodiments, the *Enterococcus* bacteria might comprise *Enterococcus azikeevi* strain EO-07 with the Deposit Number of CGMCC No. 18437 or an *Enterococcus azikeevi* strain comprising the 16S rDNA sequence of SEQ ID NO: 8.

In some embodiments, the *Alcaligenes* bacteria might comprise *Alcaligenes faecalis* strain EO-05 with the Deposit Number of CGMCC No. 18435 or an *Alcaligenes faecalis* strain comprising the 16S rDNA sequence of SEQ ID NO: 1.

The degradation chamber of the third microbiological degradation system 23 may be located downstream of the degradation chamber of the second microbiological degradation system 22, and may contain aerobic bacteria that may include any one or more microorganisms selected from the group consisting of *Acetobacter peroxydans*, *Escherichia coli*, *Cycloclasticus*, *Bacillus*, and *Pseudomonas aeruginosa*. The aerobic bacteria in the degradation chamber of the third microbiological degradation system 23 can grow under aerobic conditions using ethylene oxide as a carbon source, thereby degrading the ethylene oxide remaining in the secondary degradation exhaust liquor to obtain a tertiary degradation exhaust liquor.

In some embodiments, the *Acetobacter peroxydans* bacteria might comprise *Acetobacter peroxydans* strain EO-01 with the Deposit Number of CGMCC No. 18431 or an *Acetobacter peroxydans* strain comprising the 16S rDNA sequence of SEQ ID NO: 2.

In some embodiments, the *Bacillus* bacteria might comprise *Bacillus subtilis* strain EO-03 with the Deposit Number of CGMCC No. 18433 or a *Bacillus subtilis* strain comprising the 16S rDNA sequence of SEQ ID NO: 4.

The anaerobic bacteria, the facultative bacteria, and the aerobic bacteria may be ethylene oxide dominant degradation strains that may be screened, induced, and acclimated with ethylene oxide. By utilizing the ethylene oxide dominant degradation strains to degrade ethylene oxide, effects such as safety, high efficiency, and environmental protection can be achieved.

Although FIG. 1 shows and describes above that the three microbiological degradation systems 2 may be connected sequentially via a pipe, it will be appreciated by those skilled in the art that the present disclosure may be carried out with any two of the three microbiological degradation systems 2 being fluidly connected via a pipe in a different sequence, or with the three microbiological degradation systems 2 being fluidly connected via a pipe in a different sequence from the above description, and that these alternative solutions may also achieve the object of the present disclosure.

The third microbiological degradation system 23 may be further provided with a second gas inlet 231 and a second gas outlet 232, with the first gas outlet 103 being in fluid communication with the second gas inlet 231 via a pipe (e.g., via a first pipe, as described above, or the like), so that residual gas in the ethylene oxide exhaust gas, after the ethylene oxide has been adsorbed, may be introduced into the third microbiological degradation system 23.

As shown in FIG. 1, the microbiological treatment system 1000 may further include a recovery system comprising a clarification tank 5. The clarification tank 5 may include a liquid inlet that may be in fluid communication with the liquid outlet of the degradation chamber of the third microbiological degradation system 23 via a pipe to receive the tertiary degradation exhaust liquor from the third microbiological degradation system 23. The clarification tank 5 may further include a liquid outlet that may be in fluid communication with the liquid storage tank 3 via a pipe so that the degraded liquid (e.g., degraded water, or the like) having little or no ethylene oxide may be recovered in the liquid storage tank 3, and may be further circulated into the hydration system 1. The clarification tank 5 may further include a sludge outlet 501 that may be in fluid communication with the liquid inlet of the first microbiological degradation system 21 via a sludge pipe 502.

During the operation of the microbiological treatment system 1000 according to the present embodiment, the ethylene oxide exhaust gas may be introduced into the gas-liquid mixing chamber 106 of the hydration system 1 via the gas inlet pipe 107, and may be dispersed from the gas spraying holes 108. Water (or other suitable liquid) may enter the gas-liquid mixing chamber 106 from the liquid storage tank 3 via the liquid inlet pipe 111, and may be dispersed from the water spraying holes 112, forming descending liquid mists and/or droplets (e.g., water mists and/or droplets, or the like). The dispersed ethylene oxide exhaust gas may ascend, and may be multi-dispersed through the first gas disperser, the second gas disperser, and the third gas disperser (collectively, "the gas dispersers 109" or the like) while ascending. The dispersed or multi-dispersed ethylene oxide exhaust gas, if and when sufficiently contacted with the descending liquid mists and/or droplets (e.g., water mists and/or droplets, or the like) such that the ethylene oxide in the ethylene oxide exhaust gas may be absorbed by the water, may thereby produce an ethylene oxide exhaust liquor. The ethylene oxide exhaust liquor may be contacted again with the ethylene oxide exhaust gas that was multi-dispersed through the first gas disperser, the second gas disperser, and the third gas disperser during the descending process, and more ethylene oxide may be absorbed to form a high concentration of the ethylene oxide exhaust liquor, which may eventually be collected in the liquid storage chamber 117.

The ethylene oxide exhaust liquor that is produced in the hydration system 1 may be discharged from the first liquid outlet 105 and may enter the buffer tank 4 via a pipe through the second liquid inlet 401 in the buffer tank 4 for temporary storage. The ethylene oxide exhaust liquor may then be discharged from the second liquid outlet 402 to the first microbiological degradation system 21. The ethylene oxide in the ethylene oxide exhaust liquor may be degraded by anaerobic bacteria as a carbon source under anaerobic conditions to obtain a primary degradation exhaust liquor. The primary degradation exhaust liquor may be discharged to the second microbiological degradation system 22 via a pipe, and the ethylene oxide remaining in the primary degradation exhaust liquor may be further degraded by facultative bacteria as a carbon source under hypoxic conditions to obtain the secondary degradation exhaust liquor. The secondary degradation exhaust liquor may enter the third microbiological degradation system 23 via a pipe, and the ethylene oxide remaining in the secondary degradation exhaust liquor may be further degraded by aerobic bacteria as a carbon source under aerobic conditions to obtain the tertiary degradation exhaust liquor. The tertiary degradation exhaust liquor may be discharged to the clarification tank 5 via a pipe. After standing for clarification, the aqueous solution, such as water or other suitable liquid, in the clarification tank 5 may be recovered into the liquid storage tank 3 and may then be circulated back to the hydration system 1, thus realizing the circulation of water (or other suitable liquid).

During the operation of the hydration system 1, after the ethylene oxide exhaust gas has been absorbed by the water (or other suitable liquid) in multiple stages, the ethylene oxide exhaust gas may contain ethylene oxide having a decreasing concentration, and the residual gas may pass through the water baffle 115, where the water (or other suitable liquid) that is mixed therein may be trapped. Then, the residual gas may continue to pass through the first gas outlet 103 guided by the gas guide plate 116, and may be introduced into the third microbiological degradable system 23 via the second gas inlet 231 from the pipe to generate bubbles to increase aeration, thereby supplying oxygen to the aerobic bacteria in the third microbiological degradable system 23. Finally, the residual gas may be discharged from the second gas outlet 232.

Figure 2:
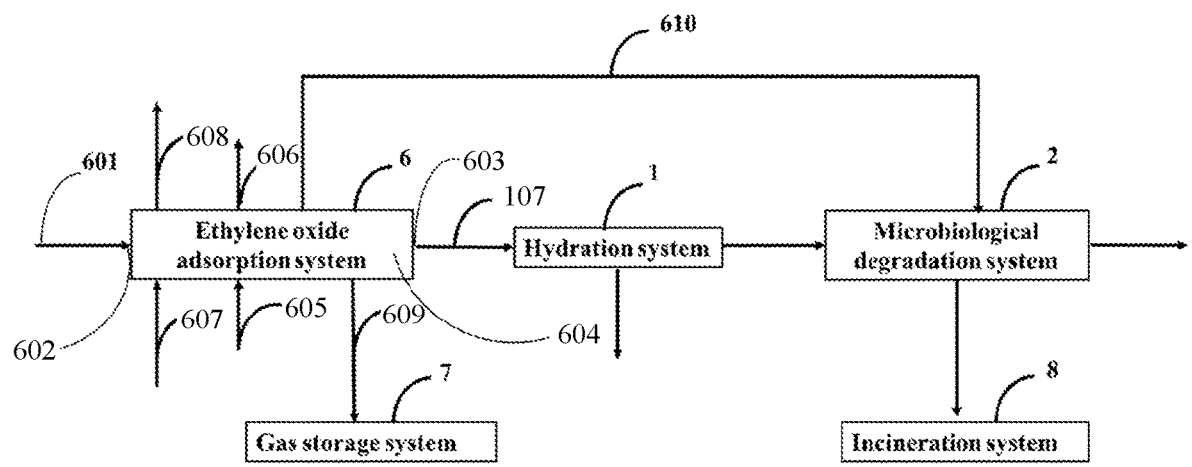
FIG. 2 is a schematic diagram depicting a microbiological treatment system including an adsorption system according to another embodiment of the present disclosure.

FIG. 2 shows an alternative microbiological treatment system 1000' including an ethylene oxide adsorption system according to another embodiment of the present disclosure. The microbiological treatment system 1000' may include an ethylene oxide adsorption system 6. The ethylene oxide adsorption system 6 may include a gas passage 601, a third gas inlet 602, and a third gas outlet 603. The third gas inlet 602 and the third gas outlet 603 may be in fluid communication with the gas passage 601. The third gas inlet 602 may be configured to introduce the ethylene oxide exhaust gas, while the third gas outlet 603 may be in fluid communication with the first gas inlet 102 via the gas inlet pipe 107 to discharge the ethylene oxide exhaust gas that has been subjected to the adsorption treatment.

An adsorbent material 604 may be provided in the gas passage 601. The adsorbent material 604 may be a porous structure. For example, the adsorbent material 604 may include any one or more materials selected from the group consisting of a coconut shell activated carbon, a columnar activated carbon, and an activated carbon fiber. Initial treatment of the ethylene oxide exhaust gas using these easily available adsorbent materials may enable the reduction of the costs for ethylene oxide exhaust gas treatment.

The ethylene oxide adsorption system 6 may further include an interlayer (not shown) surrounding the gas passage 601, a cold water inlet pipe 605 for inflow of cold water, a cold water outlet pipe 606 for outflow of cold water, a hot water inlet pipe 607 for inflow of hot water, and a hot water outlet pipe 608 for outflow of hot water that may be in fluid communication with the interlayer.

The ethylene oxide adsorption system 6 may further include a gas recovery pipe 609 that may be in fluid communication with the gas passage 601. The gas recovery pipe 609 may be fluidly connected to the gas storage system 7.

The ethylene oxide adsorption system 6 may further include a solid recovery pipe 610, which may be fluidly connected to the one or more microbiological degradation systems 2, for example, the third microbiological degradation system 23, or the like.

Although FIG. 2 illustrates the microbiological treatment system 1000' of the present disclosure including the ethylene oxide adsorption system 6, it will be appreciated by those skilled in the art that the microbiological treatment system 1000 of the present disclosure without the ethylene oxide adsorption system 6, as shown in FIG. 1, can also achieve the objects of the present disclosure.

In a specific embodiment, during the operation of the microbiological treatment system 1000' including the ethylene oxide adsorption system 6 according to the present disclosure, the ethylene oxide exhaust gas may enter the ethylene oxide adsorption system 6 via the third gas inlet 602, and may be adsorbed by the adsorbent material 604. When the ethylene oxide exhaust gas has been adsorbed by the adsorbent material 604, cold water may be introduced through the cold water inlet pipe 605 and may be discharged through the cold water outlet pipe 606, thereby improving the adsorption effect of the adsorbent material 604. The ethylene oxide exhaust gas that has been subjected to adsorption treatment may be introduced from the third gas outlet 603 into the hydration system 1 via the gas inlet pipe 107 and, as described above, may be absorbed in the hydration system 1 by an aqueous solution, such as water or other suitable liquid, resulting in an ethylene oxide exhaust liquor and a residual gas. The residual gas may be discharged via a pipe into the external environment or into the third microbiological degradation system 23, and finally may be discharged through the second gas outlet 232. Meanwhile, the ethylene oxide exhaust liquor may enter the one or more microbiological degradation systems 2 for degradation, as described in detail above.

During the adsorption process, after the adsorption material 604 in the ethylene oxide adsorption system 6 reaches a saturated state, the valve 120 in the gas inlet pipe 107 may be closed, hot water may be introduced through the hot water inlet pipe 607 and may be discharged through the hot water outlet pipe 608. The adsorption material 604 may thus be desorbed to obtain the desorbed adsorption material 604 and clean ethylene oxide. The clean ethylene oxide may enter the gas storage system 7 through the gas recovery pipe 609 for storage. The desorbed adsorbent material 604 may be introduced into the one or more microbiological degradation systems 2, for example, the third microbiological degradation system 23, through the solid recovery pipe 610. The residual ethylene oxide in the desorbed adsorbent material 604 may be degraded by aerobic microorganisms as a carbon source, and the treated desorbed adsorbent material 604, as well as the (tertiary) degradation exhaust liquor (produced by the three microbiological degradation systems 21, 22, and 23 (as described in detail above)), may be discharged into the clarification tank 5 (as shown in FIG. 1). After the treated desorbed adsorbent material 604, as well as the (tertiary) degradation exhaust liquor, has (have) been settled and clarified in the clarification tank 5, the obtained activated sludge may be introduced into the first microbiological degradation system 21 through the sludge pipe 502 (as shown in FIG. 1), and the obtained solid waste may be introduced into the incineration system 8 through a pipe, and may be subjected to incineration treatment.

In the present disclosure, by using the above-described hydration system 1 and various bacterial, microbiological, and/or ethylene oxide degradation strains, a safe and efficient treatment for ethylene oxide in ethylene oxide sterilization exhaust gases may be achieved, which produces minimal or no pollution or contamination to the environment. The ethylene oxide may be recovered by the adsorption system, thereby improving the utilization rate of the ethylene oxide. In addition, by performing the microbiological treatment for the waste solids and the exhaust liquor in the degradation system, and then performing incineration, the waste residue may be reduced.

Ethylene oxide treatment experiments were carried out using the microbiological treatment system 1000 or 1000' of the present disclosure, as summarized below. An ethylene oxide sterilization exhaust gas was introduced into the hydration system 1 of the present disclosure using water as an aqueous solution, and the ethylene oxide exhaust liquor that was obtained after the ethylene oxide sterilization exhaust gas was absorbed by the water entered into three microbiological degradation systems for degradation. The results obtained are shown in Table 1 below:

TABLE 1

| Experiment number | Initial EO concentration in ethylene oxide exhaust liquor in hydration system 1 | EO concentration after treatment in the first MDG | EO concentration after treatment in the second MDG | EO concentration after treatment in the third MDG | EO concentration for Discharge | Treatment efficiency |
|---|---|---|---|---|---|---|
| Example 1 | 100 mg/L | 36.15 mg/L | 13.51 mg/L | 3.24 mg/L | 3.24 mg/L | 96.76% |
| Example 2 | 200 mg/L | 70.05 mg/L | 28.34 mg/L | 5.98 mg/L | 5.98 mg/L | 97.01% |
| Example 3 | 400 mg/L | 128.31 mg/L | 55.17 mg/L | 20.36 mg/L | 20.36 mg/L | 94.91% |
| Example 4 | 800 mg/L | 325.16 mg/L | 105.78 mg/L | 35.86 mg/L | 35.86 mg/L | 95.52% |

\* EO: Ethylene oxide
\* MDG: Microbiological degradation system
\* The above concentrations were measured at the liquid outlets of each system.

The above-listed treatment efficiency was calculated according to the following formula:

Ethylene oxide treatment efficiency=((initial EO concentration in exhaust liquor−EO concentration for Discharge)/initial EO concentration in exhaust liquor)×100%.

It can be seen from Table 1 above, the ethylene oxide exhaust liquor upon the treatment in the microbiological treatment system 1000 or 1000' according to the present disclosure (including the first microbiological degradation system 21, the second microbiological degradation system 22 and the third microbiological degradation system 23 that may be sequentially connected) has a treatment efficiency of between about 94.91% and about 97.01%. Therefore, the microbiological treatment system 1000 or 1000' according to the present disclosure can significantly reduce the environmental hazards of the ethylene oxide.

The present disclosure may further include the following embodiments.

Embodiment 1

A water adsorption microbiological treatment system for treatment of ethylene oxide sterilization gas might include an ethylene oxide sterilization waste or exhaust gas pipe, a hydration system, a buffer tank, an anaerobic microorganism ethylene oxide degradation system, a facultative microorganism ethylene oxide degradation system, an aerobic microorganism ethylene oxide degradation system, a clarification tank, a sludge pipe, a liquid storage tank, and a gas outlet pipe. The hydration system, the buffer tank, the anaerobic microorganism ethylene oxide degradation system, the facultative microorganism ethylene oxide degradation system, the aerobic microorganism ethylene oxide degradation system, the clarification tank, and the liquid storage tank may be sequentially fluidly connected by one or more pipes, and the hydration system may be fluidly connected to the liquid storage tank. The ethylene oxide sterilization waste or exhaust gas pipe may be fluidly connected to the hydration system, and the hydration system may be fluidly connected to the aerobic microorganism ethylene oxide degradation system via the gas outlet pipe. The sludge pipe may be disposed between the buffer tank and the anaerobic microorganism ethylene oxide degradation system and may be fluidly connected to the clarification tank.

Embodiment 2

In the water adsorption microbiological treatment system according to Embodiment 1, the hydration system may be provided with a tower body, a reservoir, and a pump. The tower body may be disposed at a top portion of the reservoir and may be detachably or fixedly connected to the reservoir, while the pump may be fluidly connected to the tower body via a pipe. One side of the reservoir may be detachably connected to the pump, and the top portion of the reservoir may be fluidly connected to the buffer tank. A gas disperser(s) may be provided inside the reservoir, and one end of the gas disperser(s) may be fluidly connected to the ethylene oxide sterilization waste or exhaust gas pipe.

Embodiment 3

The water adsorption microbiological treatment system according to Embodiment 2 may further comprise an upper cover and at least one viewing hole. A bottom portion of the upper cover may be sequentially provided with a gas guide plate, a water baffle, a sealing gasket, and a water sprayer(s). The upper cover, the gas guide plate, the water baffle, the sealing gasket, and the water sprayer(s) may be detachably connected to the tower body. The water sprayer(s) may each include an end that may be fluidly connected to the liquid storage tank, and the other end that may be fluidly connected to the pump. The at least one viewing hole may include a first viewing hole located below the water sprayer and a second viewing hole located on the bottom portion of the inner surface of the tower body. A gas distributor or gas disperser may be arranged on the bottom portion of the first viewing hole, and the gas distributor or gas disperser and each of the at least one viewing hole may be detachably connected to the tower body.

Embodiment 4

In the water adsorption microbiological treatment system according to Embodiment 3, valves may each be provided on one of: (i) a pipe connecting the water sprayer and the liquid storage tank; (ii) a connection portion between the top portion of the tower body and the gas outlet pipe; (iii) a pipe connecting the water sprayer and the pump; (iv) a connection portion between the gas disperser and the ethylene oxide sterilization exhaust gas pipe; (v) a pipe connecting the reservoir and the pump; and (vi) a pipe connecting the reservoir and the buffer tank.

Embodiment 5

In the water adsorption microbiological treatment system according to Embodiment 1, the anaerobic microorganism ethylene oxide degradation system might contain anaerobic bacteria that may include any one or more microorganisms selected from the group consisting of *Klebsiella pneumoniae, Clostridium faecalis, Clostridium kogasensis, Clostridium acidisoli, Enterobacteriaceae*, and *Photosynthetic* bacteria.

Embodiment 6

In the water adsorption microbiological treatment system according to Embodiment 1, the facultative microorganism ethylene oxide degradation system might contain facultative bacteria that may include any one or more microorganisms selected from the group consisting of *Kurthia gibsonii, Lactobacillus, Enterococcus faecalis, Alcaligenes, Morganella morganii*, and *Enterococcus*.

Embodiment 7

In the water adsorption microbiological treatment system according to Embodiment 1, the aerobic microorganism ethylene oxide degradation system might contain aerobic bacteria that may include any one or more microorganisms selected from the group consisting of *Acetobacter peroxydans, Escherichia coli, Cycloclasticus, Bacillus*, and *Pseudomonas aeruginosa*.

Embodiment 8

In the water adsorption microbiological treatment system according to Embodiment 7, the aerobic microorganism ethylene oxide degradation system may be further provided with a gas outlet.

Embodiment 9

In the water adsorption microbiological treatment system according to any one of Embodiments 5 to 7, the anaerobic bacteria, the facultative bacteria, and the aerobic bacteria may include ethylene oxide dominant degradation strains that were screened, induced, and acclimated with ethylene oxide.

While certain features and aspects have been described with respect to exemplary embodiments, one skilled in the art will recognize that numerous modifications are possible. For example, the methods and processes described herein may be implemented using hardware components, software components, and/or any combination thereof. Further, while various methods and processes described herein may be described with respect to particular structural and/or functional components for ease of description, methods provided by various embodiments are not limited to any particular structural and/or functional architecture but instead can be implemented on any suitable hardware, firmware and/or software configuration. Similarly, while certain functionality is ascribed to certain system components, unless the context dictates otherwise, this functionality can be distributed among various other system components in accordance with the several embodiments.

Moreover, while the procedures of the methods and processes described herein are described in a particular order for ease of description, unless the context dictates otherwise, various procedures may be reordered, added, and/or omitted in accordance with various embodiments. Moreover, the procedures described with respect to one method or process may be incorporated within other described methods or processes; likewise, system components described according to a particular structural architecture and/or with respect to one system may be organized in alternative structural architectures and/or incorporated within other described systems. Hence, while various embodiments are described with—or without—certain features for ease of description and to illustrate exemplary aspects of those embodiments, the various components and/or features described herein with respect to a particular embodiment can be substituted, added and/or subtracted from among other described embodiments, unless the context dictates otherwise. Consequently, although several exemplary embodiments are described above, it will be appreciated that the disclosure is intended to cover all modifications and equivalents within the scope of the following claims.

What is claimed is:

1. A microbiological treatment system for treatment of ethylene oxide exhaust gas, comprising:

a hydration system comprising a gas-liquid mixing chamber, a first gas inlet, a first gas outlet, a first liquid inlet, and a first liquid outlet, the first gas inlet, the first gas outlet, the first liquid inlet, and the first liquid outlet being in fluid communication with the gas-liquid mixing chamber, wherein the first gas inlet is configured to introduce an ethylene oxide exhaust gas into the gas-liquid mixing chamber to mix with an aqueous solution to form an ethylene oxide exhaust liquor, and the first liquid outlet is configured to discharge the ethylene oxide exhaust liquor; and at least two microbiological degradation systems, each of the microbiological degradation systems comprising a degradation chamber containing degradation bacteria that are selected from any one of anaerobic bacteria, facultative bacteria, and aerobic bacteria, wherein the degradation chambers of the at least two microbiological degradation systems are in fluid communication sequentially in a predetermined degradation sequence, wherein a degradation chamber that is located most upstream in the degradation sequence has a liquid inlet that is in fluid communication with the first liquid outlet of the hydration system.

2. The microbiological treatment system of claim 1, wherein the at least two microbiological degradation systems comprise:
a first microbiological degradation system, a degradation chamber of the first microbiological degradation system being located most upstream in the degradation sequence and containing anaerobic bacteria;
a second microbiological degradation system, a degradation chamber of the second microbiological degradation system being located at a position that is downstream of the degradation chamber of the first microbiological degradation system and containing facultative bacteria; and
a third microbiological degradation system, a degradation chamber of the third microbiological degradation system being located at a position that is downstream of the degradation chamber of the second microbiological degradation system and containing aerobic bacteria.

3. The microbiological treatment system of claim 2, wherein the degradation chamber of the third microbiological degradation system is provided with a second gas inlet and a second gas outlet, and the first gas outlet is in fluid communication with the second gas inlet via a first pipe.

4. The microbiological treatment system of claim 1, wherein the anaerobic bacteria include any one or more microorganisms selected from the group consisting of *Klebsiella pneumoniae, Clostridium faecalis, Clostridium kogasensis, Clostridium acidisoli, Enterobacteriaceae*, and *Photosynthetic* bacteria; the facultative bacteria include any one or more microorganisms selected from the group consisting of *Kurthia gibsonii, Lactobacillus, Enterococcus faecalis, Alcaligenes, Morganella morganii*, and *Enterococcus*; and the aerobic bacteria include any one or more microorganisms selected from the group consisting of *Acetobacter peroxydans, Escherichia coli, Cycloclasticus, Bacillus*, and *Pseudomonas aeruginosa*.

5. The microbiological treatment system of claim 4, wherein the anaerobic bacteria, the facultative bacteria, and the aerobic bacteria are ethylene oxide dominant degradation strains that are screened, induced, and acclimated with ethylene oxide.

6. The microbiological treatment system of claim 1, further comprising a recovery system that is in fluid communication with a liquid outlet of the degradation chamber that is located most downstream in the degradation sequence.

7. The microbiological treatment system of claim 6, wherein the recovery system comprises a clarification tank and a liquid storage tank, wherein the clarification tank has a liquid inlet that is in fluid communication with the liquid outlet of the degradation chamber that is located most downstream in the degradation sequence via a second pipe, and a liquid outlet that is in fluid communication with the liquid storage tank via a third pipe, wherein the hydration system is in fluid communication with the liquid storage tank through the first liquid inlet.

8. The microbiological treatment system of claim 7, wherein the clarification tank has a sludge outlet that is in fluid communication with a liquid inlet of the degradation chamber that is located most upstream in the degradation sequence via a sludge pipe.

9. The microbiological treatment system of claim 1, further comprising a buffer tank having a second liquid inlet and a second liquid outlet, wherein the first liquid outlet is in fluid communication with the second liquid inlet, wherein the second liquid outlet is in fluid communication with the liquid inlet of the degradation chamber that is located most upstream in the degradation sequence.

10. The microbiological treatment system of claim 1, further comprising an ethylene oxide adsorption system comprising a gas passage, a third gas inlet, and a third gas outlet, the third gas inlet and the third gas outlet being in fluid communication with the gas passage, wherein an adsorbent material is provided in the gas passage, and wherein the third gas inlet is configured to introduce ethylene oxide exhaust gas, and is in fluid communication with the first gas inlet.

11. The microbiological treatment system of claim 10, wherein the adsorbent material includes any one or more materials selected from the group consisting of a coconut shell activated carbon, a columnar activated carbon, and an activated carbon fiber.

12. The microbiological treatment system of claim 10, wherein the ethylene oxide adsorption system further comprises an interlayer surrounding the gas passage, a hot water inlet pipe, a hot water outlet pipe, a cold water inlet pipe, a cold water outlet pipe, and a gas recovery pipe, the hot water inlet pipe, the host water outlet pipe, the cold water inlet pipe, and the cold water outlet pipe being in fluid communication with the interlayer, wherein the gas recovery pipe is in fluid communication with the gas passage.

13. The microbiological treatment system of claim 1, wherein the hydration system further comprises:
a tower body comprising the gas-liquid mixing chamber, wherein the first gas inlet and the first liquid outlet are located at a lower portion of the tower body, and wherein the first gas outlet and the first liquid inlet are located at an upper portion of the tower body;
a gas inlet pipe connected at the first gas inlet, wherein a portion of the gas inlet pipe extends into the gas-liquid mixing chamber, with the portion of the gas inlet pipe that is located in the gas-liquid mixing chamber being provided with a plurality of gas spraying holes; and
a liquid inlet pipe connected at the first liquid inlet, wherein a portion of the liquid inlet pipe extends into the gas-liquid mixing chamber, with the portion of the liquid inlet pipe that is located in the gas-liquid mixing chamber being provided with a plurality of liquid spraying holes.

14. The microbiological treatment system of claim 13, wherein the hydration system further comprises a water baffle disposed in the gas-liquid mixing chamber, an edge of the water baffle being connected to a wall of the gas-liquid mixing chamber, wherein the water baffle is located between the liquid inlet pipe and the first gas outlet, and wherein the water baffle is provided with an air hole.

15. The microbiological treatment system of claim 14, wherein the hydration system further comprises a gas guide plate disposed in the gas-liquid mixing chamber, an edge of the gas guide plate being connected to the wall of the gas-liquid mixing chamber, wherein the gas guide plate is located between the first gas outlet and the water baffle, and the gas guide plate is provided with a gas guiding hole.

16. The microbiological treatment system of claim 15, wherein both of the water baffle and the gas guide plate are funnel-shaped.

17. The microbiological treatment system of claim 13, wherein the hydration system further comprises a circulation pipeline located outside the tower body and a pump mounted in the circulation pipeline, wherein the circulation pipeline has an inlet that is in fluid communication with the first liquid outlet, and wherein the circulation pipeline has an outlet that extends into the gas-liquid mixing chamber and is in fluid communication with the liquid inlet pipe.

18. A water adsorption microbiological treatment system for treatment of ethylene oxide sterilization gas, comprising:
- an ethylene oxide sterilization exhaust gas pipe;
- a hydration system;
- a buffer tank;
- a first microbiological degradation system;
- a second microbiological degradation system;
- a third microbiological degradation system;
- a clarification tank;
- a sludge pipe;
- a liquid storage tank;
- and a gas outlet pipe;
- wherein the hydration system, the buffer tank, the first microbiological degradation system, the second microbiological degradation system, the third microbiological degradation system, the clarification tank, and the liquid storage tank are sequentially fluidly connected via at least one pipe, and the hydration system is fluidly connected to the liquid storage tank, and
- wherein the ethylene oxide sterilization exhaust gas pipe is fluidly connected to the hydration system, wherein the hydration system is fluidly connected to the third microbiological degradation system via the gas outlet pipe, and wherein the sludge pipe is disposed between the buffer tank and the first microbiological degradation system and is fluidly connected to the clarification tank.

\* \* \* \* \*

UNITED STATES PATENT AND TRADEMARK OFFICE
CERTIFICATE OF CORRECTION

PATENT NO. : 11,136,253 B1  
APPLICATION NO. : 17/012864  
DATED : October 5, 2021  
INVENTOR(S) : Jianlong Xue et al.

Page 1 of 1

It is certified that error appears in the above-identified patent and that said Letters Patent is hereby corrected as shown below:

In the Claims

Column 34, Line 24:  
Delete: "inlet pipe, the host water outlet pipe, the cold water inlet"  
Insert: --inlet pipe, the hot water outlet pipe, the cold water inlet--

Signed and Sealed this  
Twenty-eighth Day of December, 2021

Drew Hirshfeld  
*Performing the Functions and Duties of the*  
*Under Secretary of Commerce for Intellectual Property and*  
*Director of the United States Patent and Trademark Office*